United States Patent
Ramanathan

(10) Patent No.: US 10,905,361 B2
(45) Date of Patent: Feb. 2, 2021

(54) RADIAL CHECK DEVICE

(71) Applicant: ProMedica Health System, Inc., Toledo, OH (US)

(72) Inventor: Periakaruppan Kasi Ramanathan, Ottawa Hills, OH (US)

(73) Assignee: PROMEDICA HEALTH SYSTEM, INC., Toledo, OH (US)

(*) Notice: Subject to any disclaimer, the term of this patent is extended or adjusted under 35 U.S.C. 154(b) by 906 days.

(21) Appl. No.: 15/424,046

(22) Filed: Feb. 3, 2017

(65) Prior Publication Data

US 2017/0202496 A1    Jul. 20, 2017

Related U.S. Application Data

(63) Continuation-in-part of application No. 14/882,715, filed on Oct. 14, 2015, which is a continuation-in-part of application No. PCT/US2014/036777, filed on May 5, 2014.

(60) Provisional application No. 62/064,503, filed on Oct. 16, 2014, provisional application No. 61/819,747, filed on May 6, 2013.

(51) Int. Cl.

| A61B 5/1455 | (2006.01) |
| A61B 5/0205 | (2006.01) |
| A61B 5/00 | (2006.01) |
| A61B 5/024 | (2006.01) |
| A61B 5/022 | (2006.01) |
| A61B 5/026 | (2006.01) |

(52) U.S. Cl.
CPC ...... *A61B 5/14552* (2013.01); *A61B 5/02233* (2013.01); *A61B 5/02427* (2013.01); *A61B 5/02438* (2013.01); *A61B 5/6824* (2013.01); *A61B 5/6826* (2013.01); *A61B 5/742* (2013.01); *A61B 5/7435* (2013.01); *A61B 5/7475* (2013.01); *A61B 5/022* (2013.01); *A61B 5/026* (2013.01); *A61B 5/6838* (2013.01); *A61B 5/7445* (2013.01)

(58) Field of Classification Search
CPC . A61B 5/1455; A61B 5/0261; A61B 5/14552; A61B 5/02427; A61B 5/6824; A61B 5/7445
See application file for complete search history.

(56) References Cited

U.S. PATENT DOCUMENTS

| 4,760,846 A | 8/1988 | Mers Kelly et al. |
| 5,601,597 A | 2/1997 | Arrowood et al. |
| 6,162,181 A | 12/2000 | Hynson et al. |
| 6,463,310 B1 | 10/2002 | Swedlow et al. |

(Continued)

FOREIGN PATENT DOCUMENTS

JP    05137730 A    6/1993

OTHER PUBLICATIONS

Layton et al., "Use of the Ulnar Artery as an Alternative Access Site for Cerebral Angiography", American Journal of Neuroradiology, 2006, vol. 27, pp. 2073-2074.

(Continued)

*Primary Examiner* — Eric F Winakur
(74) *Attorney, Agent, or Firm* — Michael E. Dockins; Shumaker, Loop & Kendrick, LLP

(57) ABSTRACT

A radial check device, system, and related methods are provided for accessing ulnar and/or radial flow and producing documentation or electronic records of such assessment.

20 Claims, 25 Drawing Sheets

(56) References Cited

U.S. PATENT DOCUMENTS

| | | | |
|---|---|---|---|
| 6,540,688 B1 | 4/2003 | Gingrich et al. | |
| 6,663,653 B2 | 12/2003 | Akerfeldt | |
| 6,694,821 B2 | 2/2004 | Yamakoshi et al. | |
| 8,043,223 B2 | 10/2011 | Friedman et al. | |
| 8,353,927 B2 | 1/2013 | Lampropoulos et al. | |
| 9,392,945 B2 * | 7/2016 | Al-Ali | A61B 5/14551 |
| 2006/0149153 A1 | 7/2006 | Shirasaki et al. | |
| 2006/0224058 A1 | 10/2006 | Mannheimer | |
| 2009/0163824 A1 | 6/2009 | Ide et al. | |
| 2010/0106029 A1 | 4/2010 | Fraden | |
| 2013/0037036 A1 | 2/2013 | Carlin | |
| 2015/0018869 A1 * | 1/2015 | Benz | A61B 17/135 |
| | | | 606/203 |
| 2015/0099949 A1 * | 4/2015 | Wallace | A61B 5/14551 |
| | | | 600/323 |

OTHER PUBLICATIONS

Paul et al., "Combining the Modified Allen's Test and Pulse Oximetry for Evaluating Ulnar Collateral Circulation to the Hand for Radial Artery Catheterization of the ED Patient", The California Journal of Emergency Medicine IV, 2003, vol. 4, pp. 89-91.

Vasculaperspectives, "Helix Radial Compression Device", Vascular Perspectives Ltd., 2011, vol. 4, pp. 1-4.

PCT International Search Report and Written Opinion, Application No. PCT/US14/36777, dated Sep. 8, 2014.

* cited by examiner

RADIAL CHECK DEVICE

RELATED APPLICATIONS

This is a continuation-in-part application filed under 35 U.S.C. § 111(a) of U.S. application Ser. No. 14/882,715, filed under 35 U.S.C. § 111(a) on Oct. 14, 2015, published; which claims priority to U.S. Provisional Application No. 62/064,503, filed under 35 U.S.C. § 111(b) on Oct. 16, 2014, and is a continuation-in-part application of international application PCT/US14/36777, filed under the authority of the Patent Cooperation Treaty on May 5, 2014; published; which claims priority to U.S. Provisional Application No. 61/819,747, filed under 35 U.S.C. § 111(b) on May 6, 2013. The entire disclosures of all the aforementioned applications are incorporated herein by reference for all purposes.

TECHNICAL FIELD

The invention relates generally to medical devices. More specifically, the invention is a radial check device.

BACKGROUND OF THE INVENTION

Radial artery access is being increasingly used by physicians for diagnostic and coronary procedures. In preparation for such procedures, the Allen's test (or modified plethysmography) has been used to determine the patency of the radial and ulnar arteries. This is a manual test in which a healthcare professional, usually a nurse, places his or her thumbs over the radial arteries of a patient while the patient is clenching his or her fists. This compresses the radial arteries. The patient is then asked to open his or her hands into a relaxed position. The healthcare professional then observes the color of the palms, which should normally turn pink promptly. An abnormal test occurs when the color of the palm does not return within eight seconds. This procedure is then repeated by occluding the ulnar arteries. In another form of this test, the fingers of the healthcare professional are used to occlude both the radial and ulnar arteries of the patient. Pressure on the ulnar artery is then removed while maintaining pressure on the radial site. The color of the palm is then observed. This procedure is then performed on the other arm.

In those patients that require a second procedure through the same radial site, it is often useful to perform a reverse Allen's test. In this procedure, the healthcare professional releases pressure over the radial artery rather than the ulnar artery. This may detect proximal radial artery disease/occlusion that may be asymptomatic.

Barbeau's test is another preparation procedure. This test includes the steps as follows: placing a pulse oximeter (plethysmography) on an index finger or a thumb to demonstrate a normal waveform/tracing and releasing pressure over the ulnar artery and watching the pulse oximetry tracing. The immediate return of normal waveform suggests a normal (positive) test, which is indicative of good ulnar flow and a lower risk of hand ischemia with radial catheterization. If the waveform does not immediately return, one can wait two minutes to evaluate the waveform. If the waveform returns within two minutes, then one can still consider radial catheterization.

It has been found that these tests are deficient for a variety of reasons. For example, they are done in a subjective fashion in which the healthcare professional uses his or her observation of palm color to determine the patency of the arteries. Further, they require extensive expertise and training on the part of the healthcare professional performing the tests. Finally, they do not provide a permanent record of the tests for future use.

BRIEF SUMMARY OF THE INVENTION

The invention provides a medical device that overcomes the deficiencies of the current manual tests as described above. In this regard, the radial check device according to the invention establishes a new standard of pre-procedural care for patients undergoing any type of radial artery canalization. Further, the invention provides a relatively simple automated test that generates documentation of ulnar and radial flow.

DETAILED DESCRIPTION OF THE INVENTION

Figure 1:
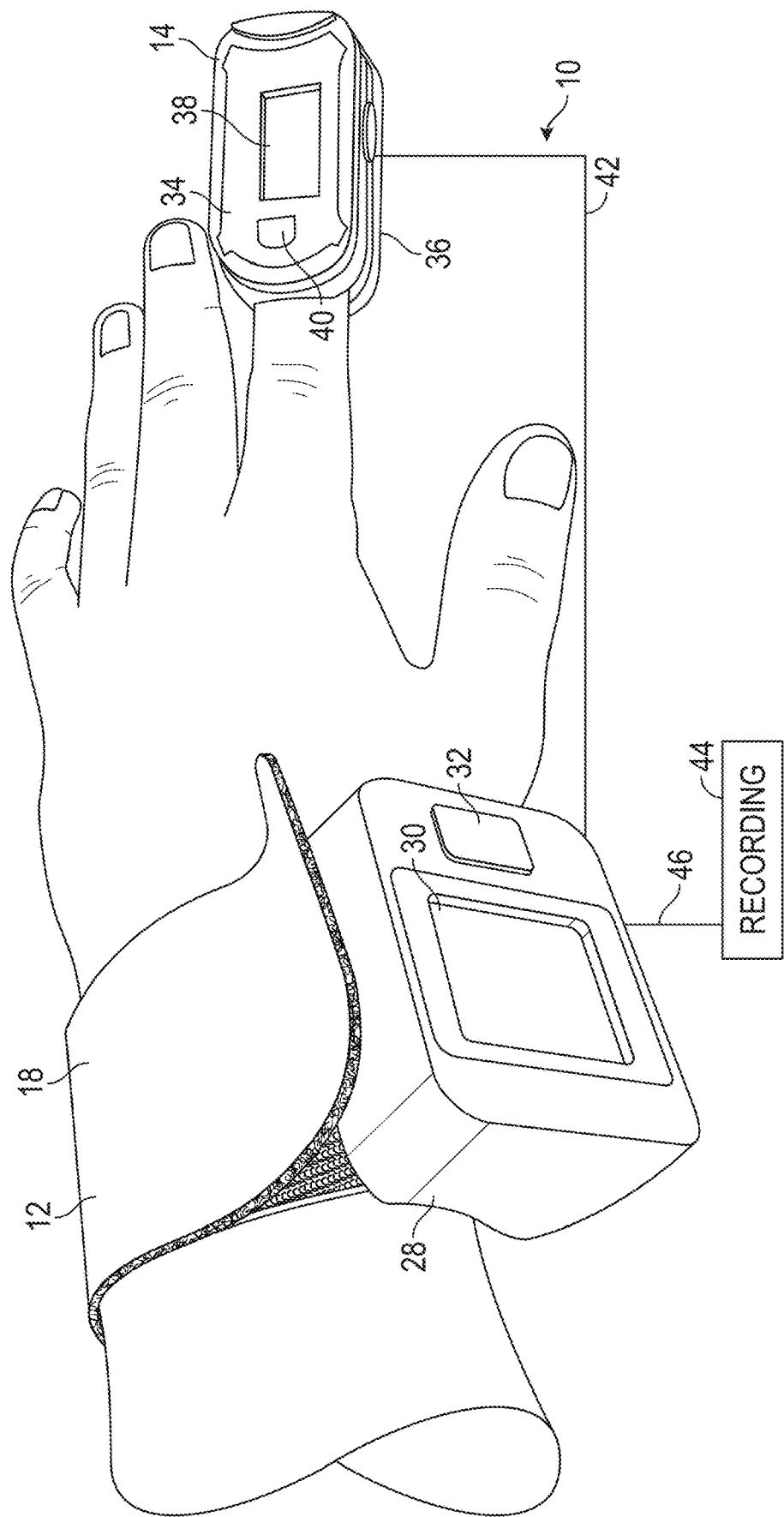
FIG. 1 is a perspective view of an embodiment of the radial check device according to the invention positioned on a patient.

The invention will now be described in detail with reference being made to the drawings. In the drawings, an embodiment of the radial check device according to the invention is indicated generally by the reference number "10." Referring to FIG. 1, the radial check device 10 has an occlusion cuff 12 configured for positioning on a patient's arm and a pulse oximeter 14 configured for positioning on a patient's finger, such as an index finger, or thumb.

Figure 2:
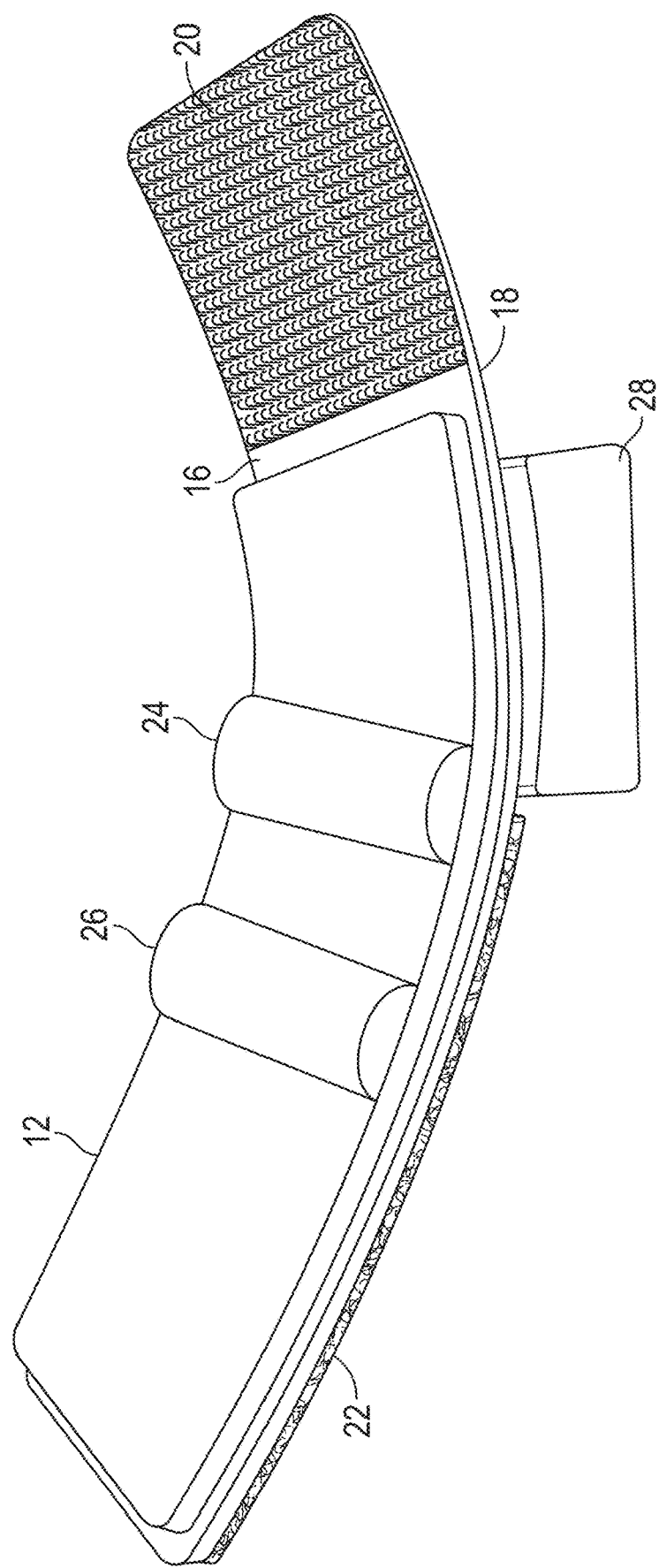
FIG. 2 is a perspective view of an embodiment of the cuff according to the invention.

As shown in FIGS. 1-2, the occlusion cuff 12 has an interior surface 16 and an exterior surface 18. A first fastener 20 is positioned on the interior surface 16 and a second fastener 22 is positioned on the exterior surface 18. For example, the first and second fasteners 20 and 22 can be hook and loop-type fasteners that adhere to each other when pressed together. The engagement of the first and second fasteners 20 and 22 position the occlusion cuff 12 on a patient's arm.

Still referring to FIGS. 1-2, the interior surface 16 of the occlusion cuff 12 includes a first inflatable portion 24 and a second inflatable portion 26. The first and second inflatable portions 24 and 26 are configured to expand and contract in order to occlude or release one or both of the radial and ulnar arteries when the occlusion cuff 12 is positioned on a patient's arm as shown in FIG. 1.

As shown in FIG. 1, the occlusion cuff 12 has a control member 28 positioned on the exterior surface 18. In an embodiment, the control member 28 includes an energy source such as a battery to actuate the first and second inflatable portions 24 and 26, a cuff display screen 30 powered by the battery, and a cuff on/off button 32. The control member 28 includes hardware, software and/or firmware configured to control the operation of the radial check device 10.

Still referring to FIG. 1, the pulse oximeter 14 includes first and second finger members 34 and 36 that are connected by a hinge or other device to allow for clamping on a patient's finger. In an embodiment, the pulse oximeter 14 includes an energy source such as a battery, a pulse oximeter display screen 38 powered by the battery, and a pulse oximeter on/off button 40. The pulse oximeter 14 includes hardware, software and/or firmware configured to control the operation of the radial check device 10.

As shown in FIG. 1, the pulse oximeter 14 is operatively connected to the control member 28 as indicated by the line 42. For example, such connection can be wired or wireless. This allows for the transmission of signals between the pulse oximeter 14 and the control member 28.

Still referring to FIG. 1, the radial check device 10 includes a recording device 44 that is operatively connected to the control member 28 as indicated by the line 46. For example, such connection can be wired or wireless. This allows for the transmission of signals between the control member 28 and the recording device 44. The recording device 44 is used to produce a record of the data being generated by the radial check device 10. For example, the recording device 44 can be a printing device that produces a paper record of the data. In another example, the recording device 44 can be an electronic device such as a computer that produces an electronic record of the data. In another example, the recording device 44 is integral with the control member 28. The record can then be entered in a patient's paper and/or electronic chart to document a test.

In use, the radial check device 10 is positioned on a patient as shown in FIG. 1. In an embodiment, the first and second inflatable portions 24 and 26 are inflated to occlude the radial and ulnar arteries, respectively. The pulse oximeter 14 provides an automated oximetry tracing to the control member 28. In an embodiment, such tracing is shown on the cuff display screen 30. The second inflatable portion 26 is then released and the oximetry tracing is transmitted to the recording device 44. The record produced by the recording device 44 is then entered in the patient's chart. In an embodiment, the radial check device 10 can perform a reverse Barbeau test to check for radial flow for patients with repeat radial procedures.

Figure 3:
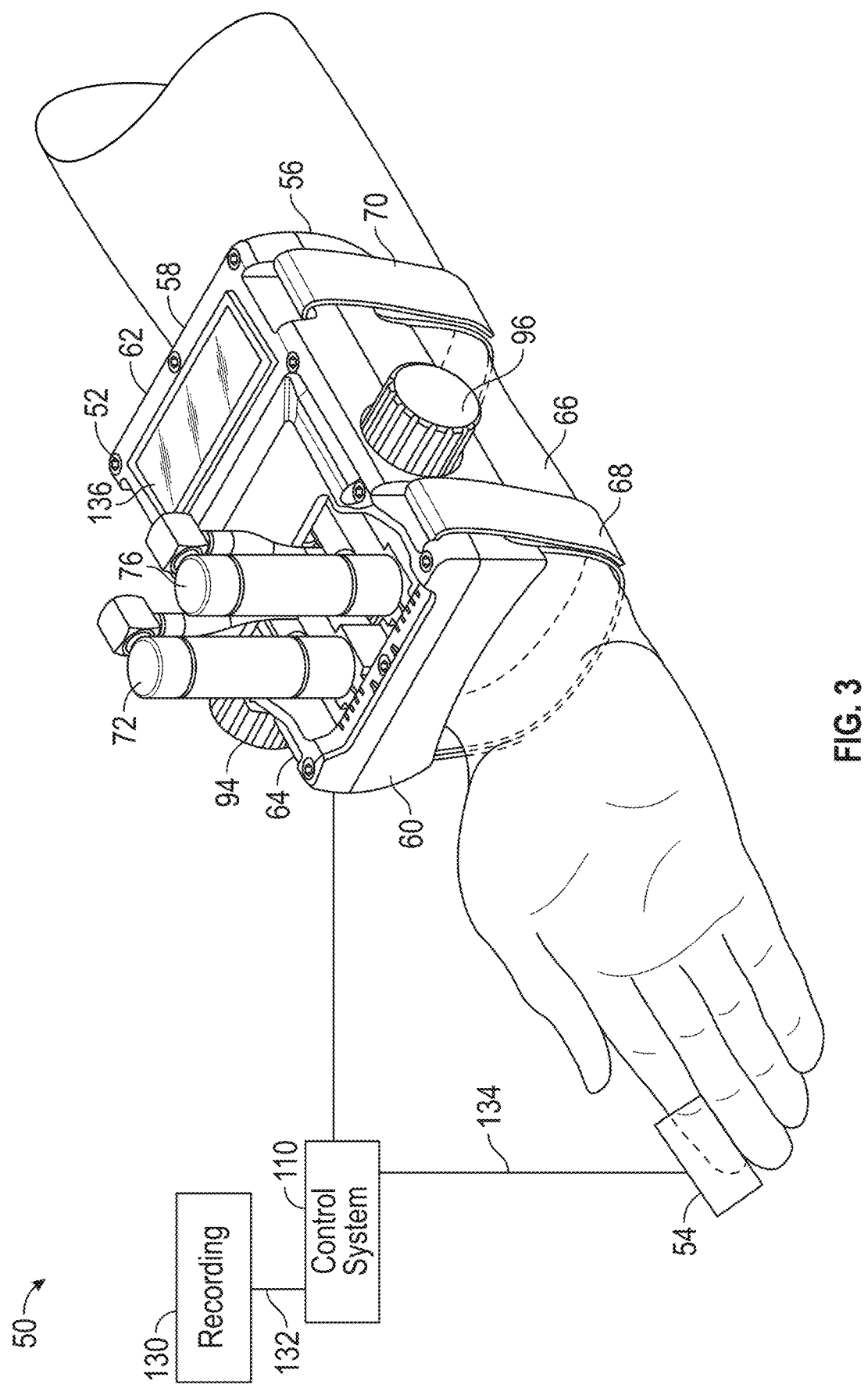
FIG. 3 is a perspective view of an alternative embodiment of the radial check device according to the invention positioned on a patient.

Referring to FIGS. 3-8B, an alternative embodiment radial check device 50 is shown and described. As shown in FIG. 3, the radial check device 50 has an occlusion cuff 52 configured for positioning on a patient's arm and a pulse oximeter 54 configured for positioning on a patient's finger, such as an index finger, or thumb. The occlusion cuff 52 has a bottom housing 56, a top housing 58, a first end 60, a second end 62, a first side 64 and a second side 66. A first strap 68 is positioned adjacent to the first end 60 and a second strap 70 is positioned adjacent to the second end 62. For example, the first and second straps 68 and 70 can include hook and loop-type fasteners that adhere to each other when pressed together. The first and second straps 68 and 70 position the occlusion cuff 52 on a patient's arm. The pulse oximeter 54 can be of the type described above with respect to pulse oximeter 14. In an embodiment, the pulse oximeter can be of a conventional type.

Referring to FIGS. 3-6, the occlusion cuff 52 includes a first actuator 72 having a first actuator tip 74 and a second actuator 76 having a second actuator tip 78. For example, as shown in this embodiment, the first and second actuators 72 and 76 can be pneumatic cylinder actuators. However, it should be understood that the first and second actuators 72 and 76 can be any suitable type of actuator that can move the first and second actuator tips 74 and 78.

Figure 4:
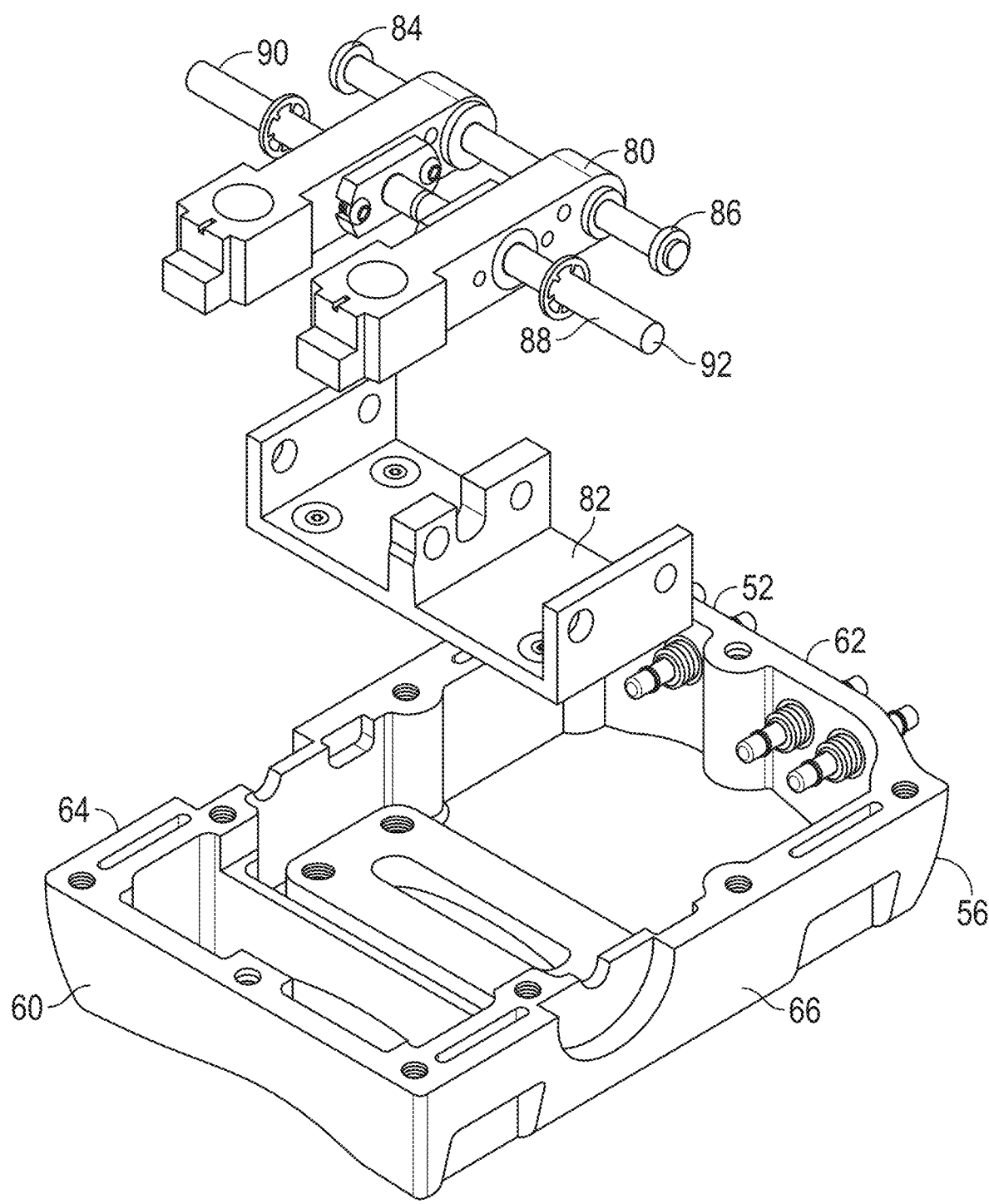
FIG. 4 is an exploded view of the radial check device shown in FIG. 3.
Figure 5:
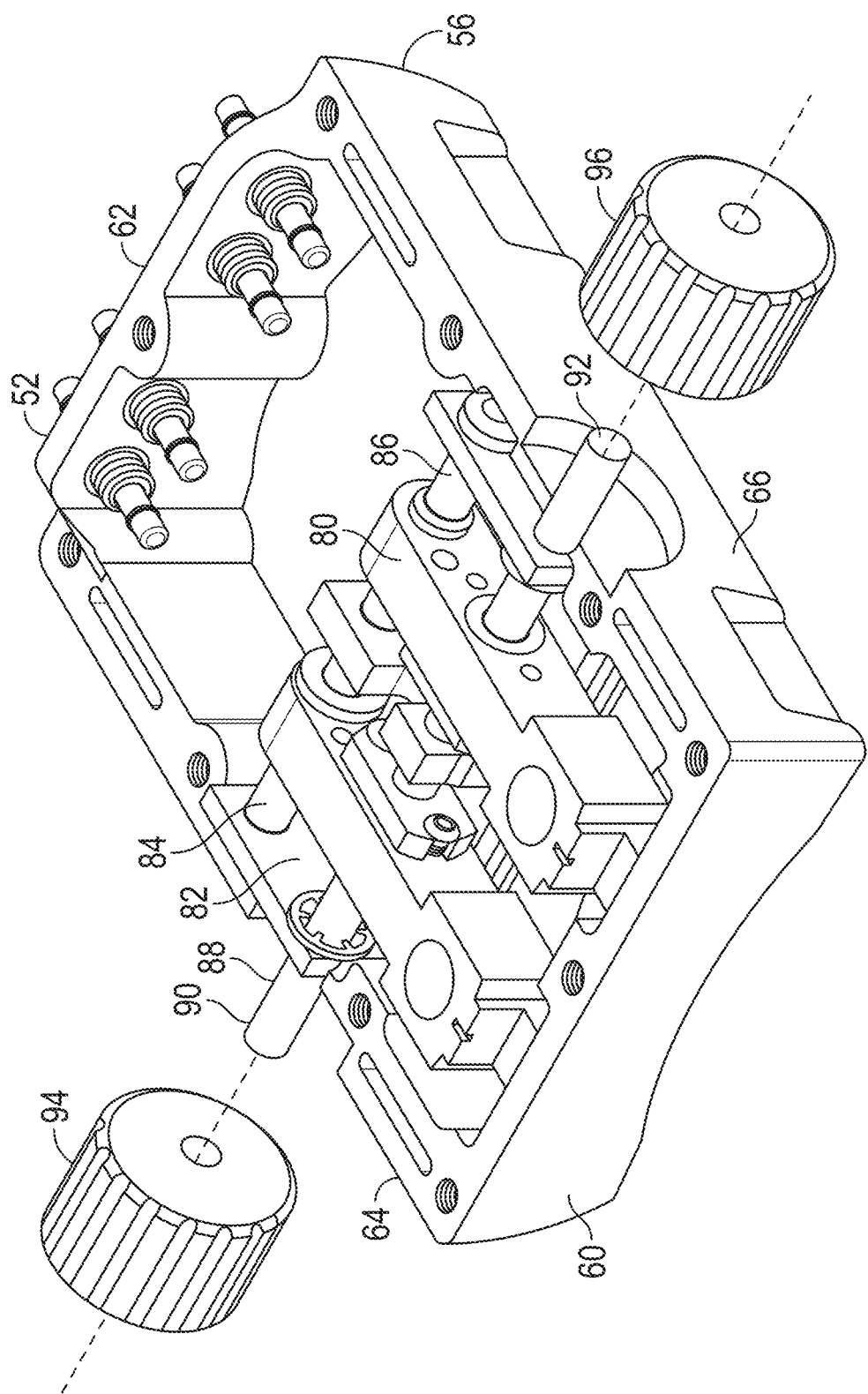
FIG. 5 is an exploded view of the radial check device shown in FIG. 3.
Figure 6:
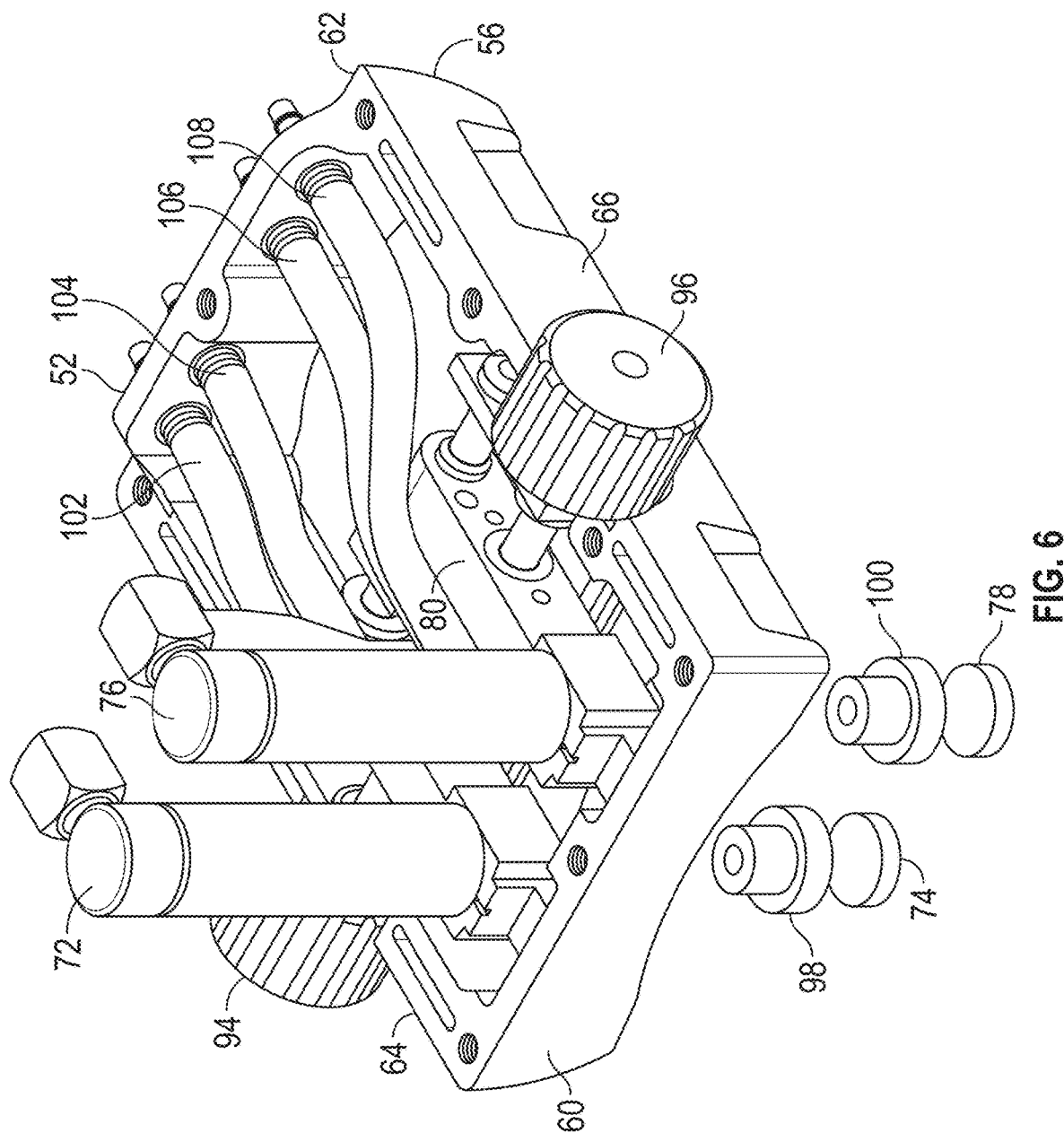
FIG. 6 is an exploded view of the radial check device shown in FIG. 3.
Figure 7:
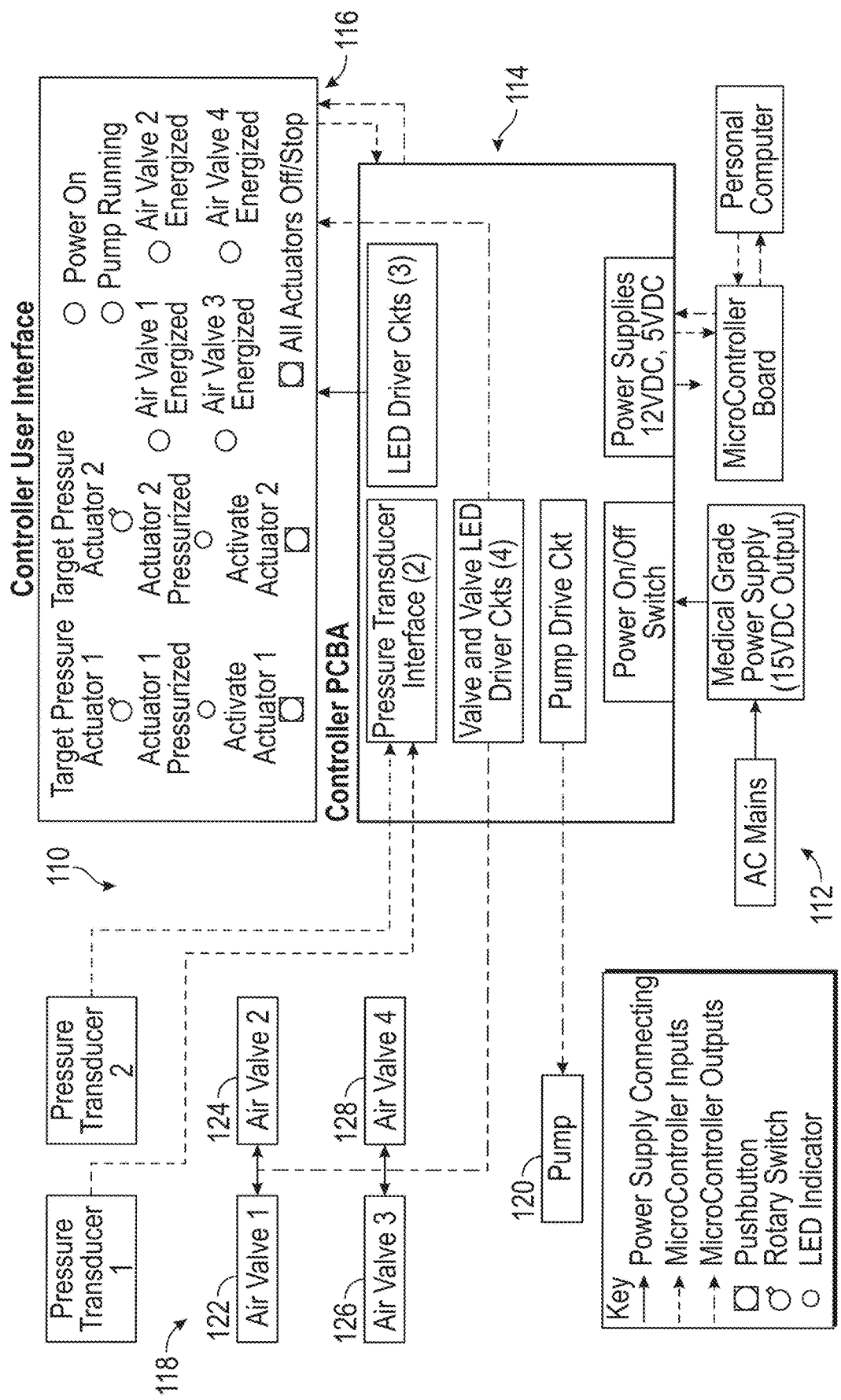
FIG. 7 is a schematic view of an embodiment of the control system for the radial check device shown in FIG. 3.
Figure 8A:
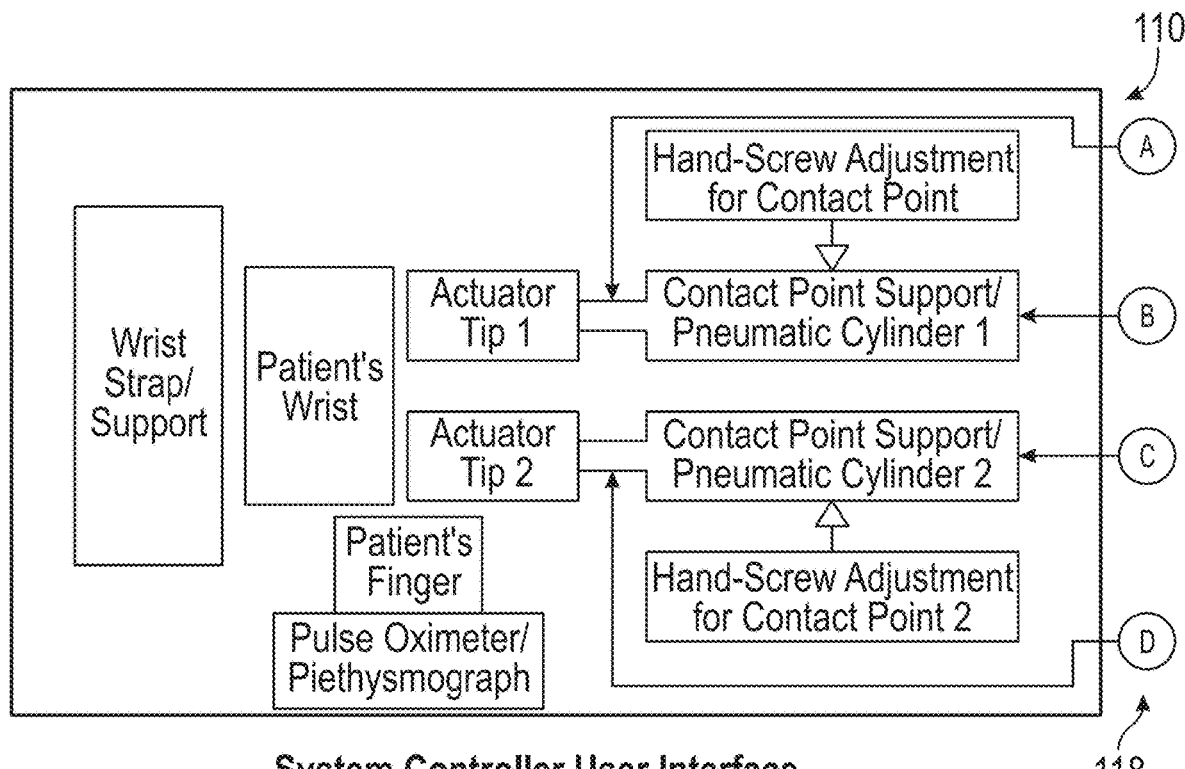
FIG. 8A is a schematic view of an embodiment of the control system for the radial check device shown in FIG. 3.
Figure 8A:
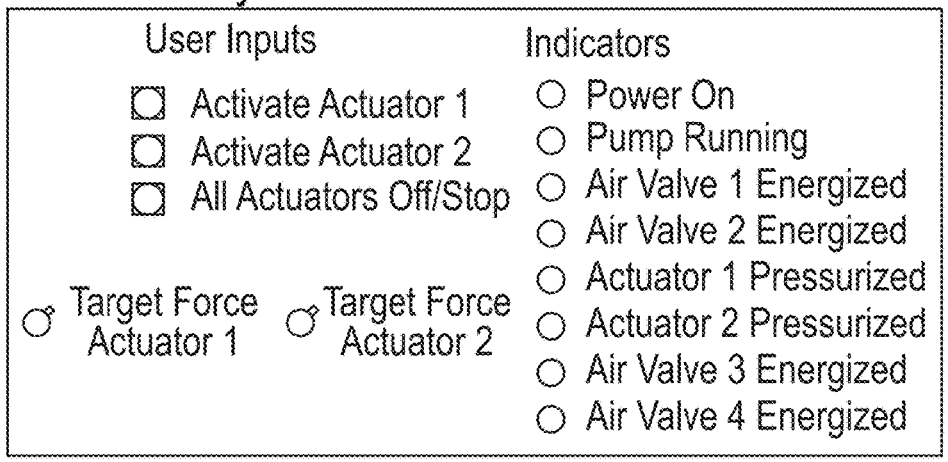
Figure 8A:
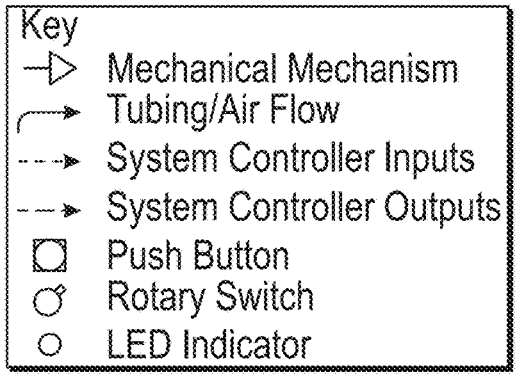
Figure 8B:
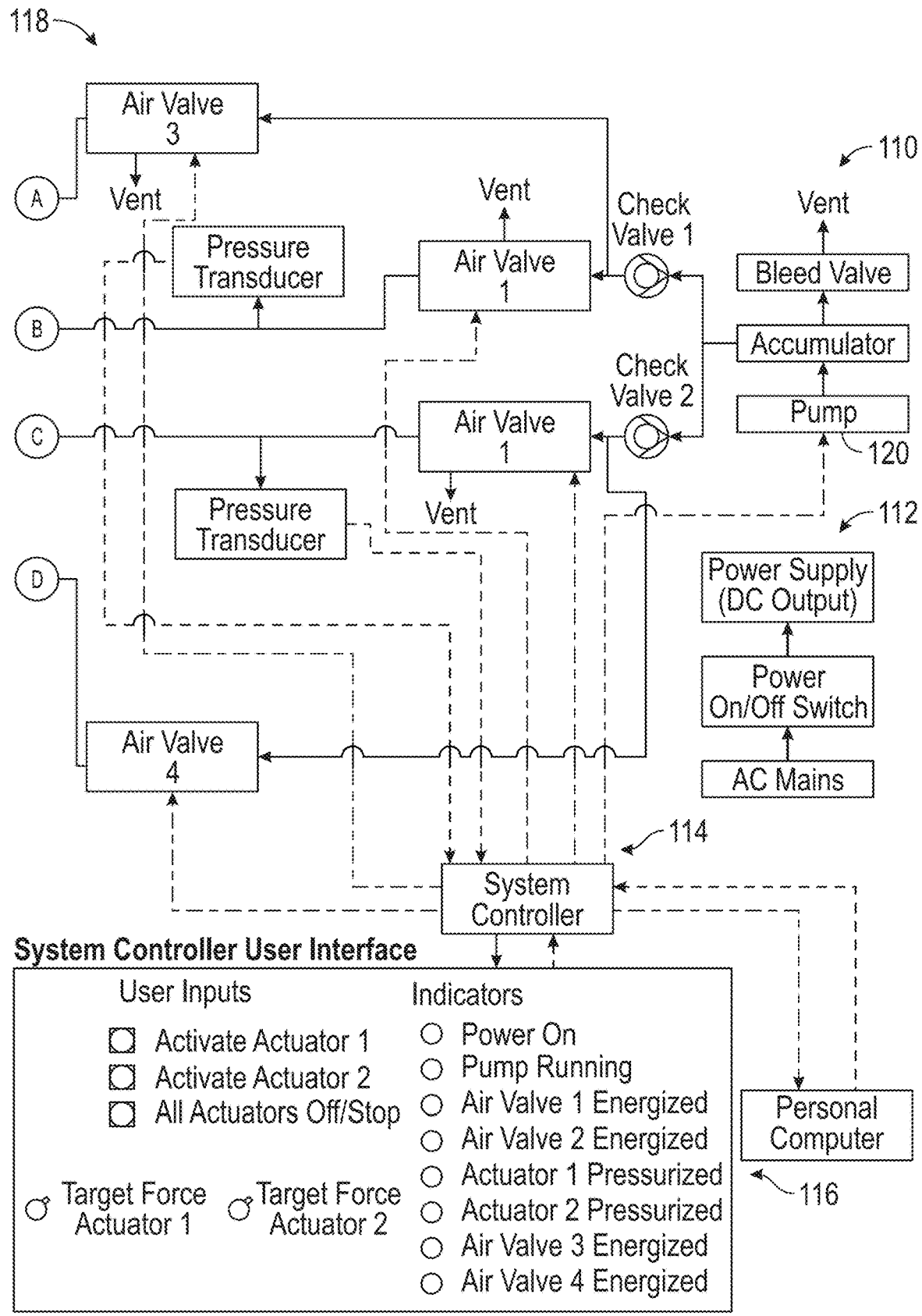
FIG. 8B is a schematic view of an embodiment of the control system for the radial check device shown in FIG. 3.

As shown in FIGS. 4-6, the first and second actuators 72 and 76 are movably mounted in the bottom housing 56 of the occlusion cuff 52. In this regard, the first and second actuators 72 and 76 are mounted on an actuator plate 80 that is pivotally positioned on a mounting frame 82 by first and second shafts 84 and 86. The actuator plate 80 includes a rod 88 that includes first and second rod ends 90 and 92 for mounting first and second knobs 94 and 96, which are positioned on the first and second sides 64 and 66, respectively, of the occlusion cuff 52. The turning of the first and second knobs 94 and 96 causes the first and second actuators 72 and 76 to be moved in order to adjust the first and second actuator tips 74 and 78 with respect to the patient's arm. As shown in FIG. 6, the first and second actuator tips 74 and 78 are positioned on first and second tip housings 98 and 100, respectively. As shown in FIG. 6, the first actuator 72 is in communication with first actuator tubes 102 and 104, and the second actuator 76 is in communication with second actuator tubes 106 and 108.

Referring to FIGS. 3, 7, 8A, and 8B, the radial check device 50 has a control system 110. As shown and described in the drawings, the control system 110 generally includes a power supply 112, a controller 114, a controller interface 116, and an actuator control system 118. The control system 110 includes hardware, software and/or firmware configured to control the operation of the radial check device 50.

As shown in FIGS. 6, 7, 8A and 8B, the actuator control system 118 includes a pump 120 in communication with first, second, third and fourth valves 122, 124, 126 and 128 that are in communication with the first and second actuator tubes 102, 104, 106 and 108. The actuation of the pump 120 controls the actuation of the first and second actuators 72 and 76. It should be understood that any suitable control system 110 can be used to control the actuation of the first and second actuators 72 and 76.

Referring to FIG. 3, the radial check device 50 can include a recording device 130 that is operatively connected to the control system 110 as indicated by the line 132. For example, such connection can be wired or wireless. This allows for the transmission of signals between the control system 110 and the recording device 130. The recording device 130 is used to produce a record of the data being generated by the radial check device 50. For example, the recording device 130 can be a printing device that produces a paper record of the data. In another example, the recording device 130 can be an electronic device such as a computer that produces an electronic record of the data. In another example, the recording device 130 is integral with the control system 110. Further, the pulse oximeter 54 can be operatively connected to the control system 110, as indicated by the line 134, for recording data. The recorded data can then be entered in a patient's paper and/or electronic chart. As shown in FIG. 3, the occlusion cuff 52 can include a cuff display screen 136 to allow for the viewing of, for example, generated data and user interface symbols.

In use, the radial check device 50 is positioned on a patient as shown in FIG. 3. In this regard, the first and second actuators 72 and 76 are positioned over, for example, the radial and ulnar arteries of the patient. The positioning of the first and second actuators 72 and 76 can be adjusted by turning the first and second knobs 94 and 96. Once the radial check device 50 is in position, first and second actuators 72 and 76 are actuated or inflated by the control system 110 to cause the first and second actuator tips 74 and 78, respectively, to occlude the radial and ulnar arteries. The pulse oximeter 54 provides an oximetry tracing. The second actuator 76 is then released and the pulse oximeter 54 provides another oximetry tracing. The oximetry tracings are read by the healthcare professional performing the test. In an embodiment, the oximetry tracings are shown on the cuff display screen 136. In an embodiment, the oximetry tracings are transmitted to the recording device 130. In an embodiment, the record produced by the recording device 130 is entered in the patient's chart. In an embodiment, the radial check device 50 can perform a reverse Barbeau test to check for radial flow for patients with repeat radial procedures.

Figure 9:
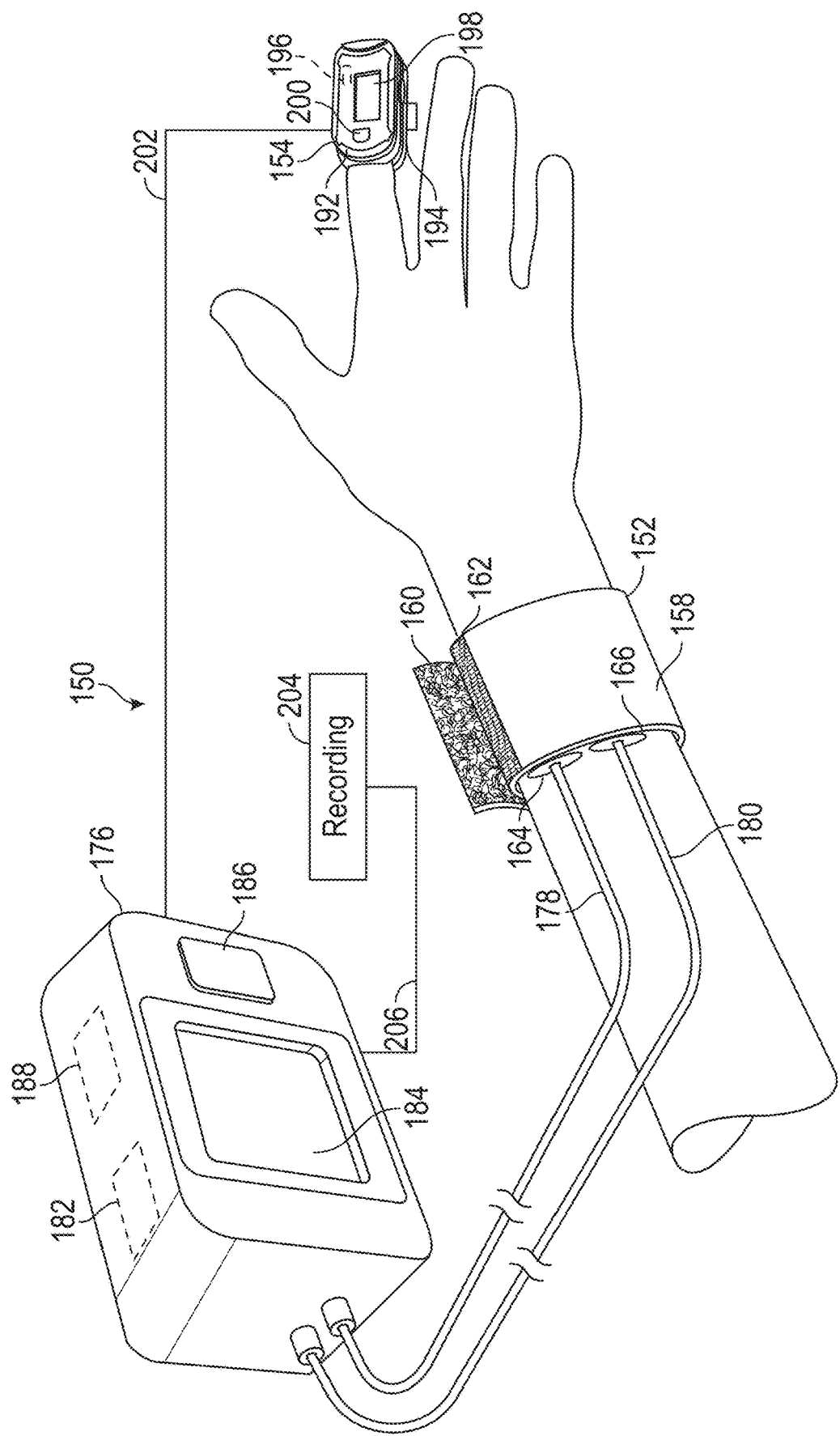
FIG. 9 is a perspective view of an alternative embodiment of the radial check device according to the invention positioned on a patient.
Figure 10:
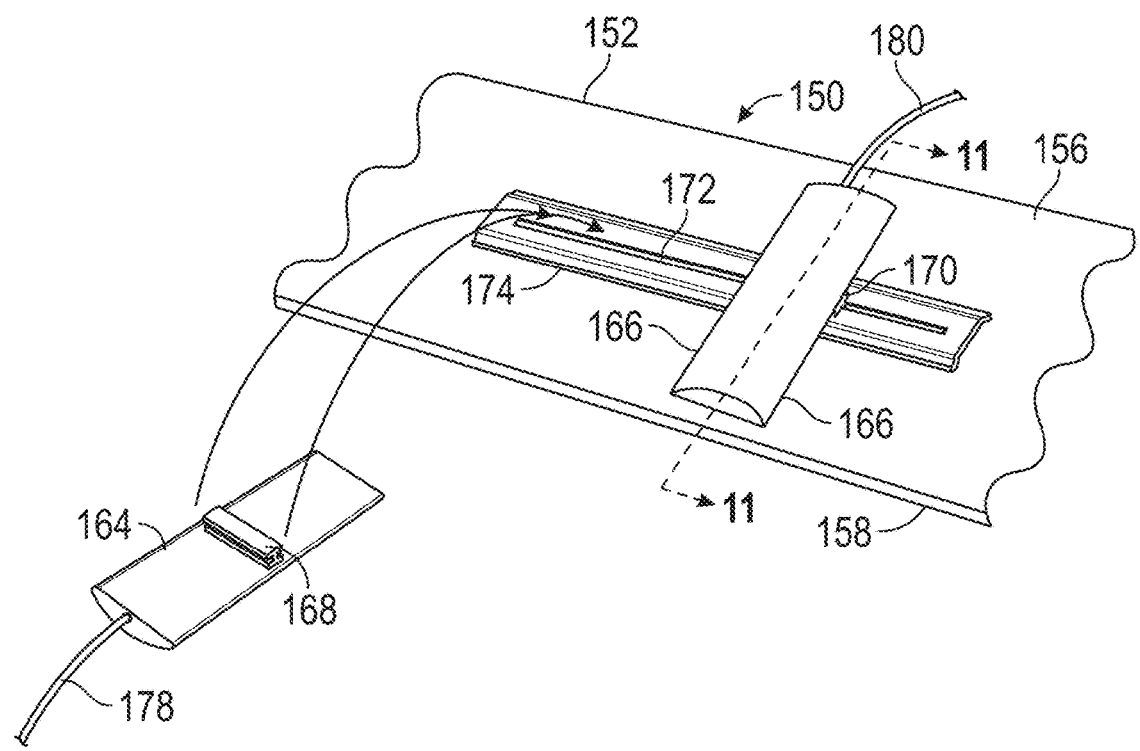
FIG. 10 is a detailed perspective view of the occlusion cuff and the first and second inflatable portions of the radial check device shown in FIG. 9.
Figure 11:
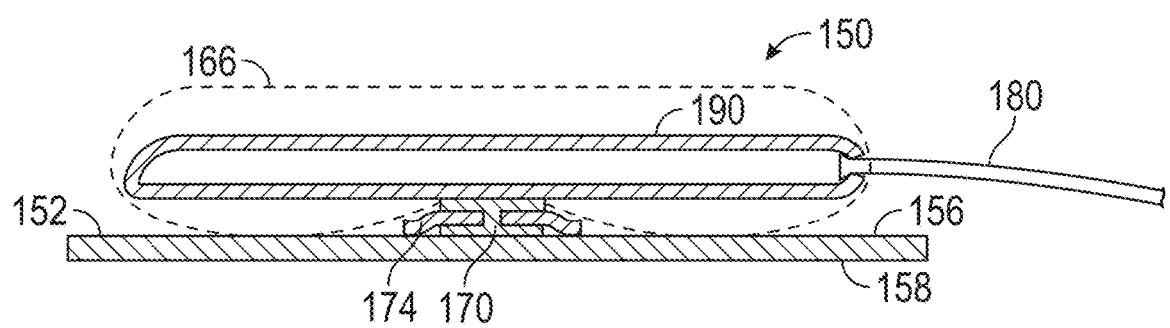
FIG. 11 is a cross-sectional view taken along line 11-11 of FIG. 10.

Referring to FIGS. 9-11, an alternative embodiment radial check device 150 is shown and described. As shown in FIG. 9, the radial check device 150 has an occlusion cuff 152 configured for positioning on a patient's arm and a pulse oximeter 154 configured for positioning on a patient's finger, such as an index finger, or thumb.

As shown in FIGS. 9-10, the occlusion cuff 152 has an interior surface 156 and an exterior surface 158. A first fastener 160 is positioned on the interior surface 156 and a second fastener 162 is positioned on the exterior surface 158. For example, the first and second fasteners 160 and 162 can be hook and loop-type fasteners that adhere to each other when pressed together. The engagement of the first and second fasteners 160 and 162 position the occlusion cuff 152 on a patient's arm.

Referring to FIGS. 9-11, the interior surface 156 of the occlusion cuff 152 includes a first inflatable portion 164 and a second inflatable portion 166. The first and second inflatable portions 164 and 166 are configured to expand and contract in order to occlude or release one or both of the radial and ulnar arteries when the occlusion cuff 152 is positioned on a patient's arm as shown in FIG. 9. In an embodiment, the first and second inflatable portions 164 and 166 are adjustable with respect to the occlusion cuff 152 to allow such inflatable portions to be properly positioned with respect to the radial and ulnar arteries. For example, the first inflatable portion 164 can include a first portion mounting member 168 and the second inflatable portion 166 can include a second portion mounting member 170 in which such mounting members are sized and adapted for sliding engagement in a slot 172 of a mounting bracket 174 that is positioned on the interior surface 156 of the occlusion cuff 152 as shown in FIGS. 10-11. In addition to this example, it should be understood that the first and second inflatable portions 164 and 166 can be adjustably positioned with respect to the occlusion cuff 152 in a variety of ways. In an embodiment, the occlusion cuff 152 and the first and second inflatable portions 164 and 166 are constructed of plastic. In an embodiment, the occlusion cuff 152 and the first and second inflatable portions 164 and 166 are disposable after use.

As shown in FIG. 9, the radial check device 150 has a control member 176 that is separate from the occlusion cuff 152. In an embodiment, the control member 176 is operatively connected to the first and second inflatable portions 164 and 166 by first and second lines or tubes 178 and 180. In an embodiment, the control member 176 includes an energy source such as a battery 182 to actuate the first and second inflatable portions 164 and 166, a cuff display screen 184 powered by the battery 182, and a cuff on/off button 186. In an embodiment, the control member 176 includes an actuation device such as a pump system 188 to provide a fluid such as air through the first and second tubes 178 and 180 to inflate or deflate the first and second inflatable portions 164 and 166. In an embodiment, each of the first and second inflatable portions 164 and 166 includes an expandable and contractible bladder 190 that is in fluid communication with the first and second tubes 178 and 180 and thus the pump system 188 as shown in FIGS. 9 and 11. The control member 176 includes hardware, software and/or firmware configured to control the operation of the radial check device 150.

Referring to FIG. 9, the pulse oximeter 154 includes first and second finger members 192 and 194 that are connected by a hinge or other device to allow for clamping on a patient's finger. In an embodiment, the pulse oximeter 154 includes an energy source such as a battery 196, a pulse oximeter display screen 198 powered by the battery 196, and a pulse oximeter on/off button 200. The pulse oximeter 154 includes hardware, software and/or firmware configured to control the operation of the radial check device 150.

As shown in FIG. 9, the pulse oximeter 154 is operatively connected to the control member 176 as indicated by the line 202. For example, such connection can be wired or wireless. This allows for the transmission of signals between the pulse oximeter 154 and the control member 176.

Still referring to FIG. 9, the radial check device 150 includes a recording device 204 that is operatively connected to the control member 176 as indicated by the line 206. For example, such connection can be wired or wireless. This allows for the transmission of signals between the control member 176 and the recording device 204. The recording device 204 is used to produce a record of the data being generated by the radial check device 150. For example, the recording device 204 can be a printing device that produces a paper record of the data. In another embodiment, the recording device 204 can be an electronic device such as a computer that produces an electronic record of the data. In another example, the recording device 204 is integral with the control member 176. The record can then be entered in a patient's paper and/or electronic chart to document the test.

In use, the radial check device 150 is positioned on a patient as shown in FIG. 9. In an embodiment, the first and second inflatable portions 164 and 166 are inflated to occlude the radial and ulnar arteries, respectively. The pulse oximeter 154 provides an automated oximetry tracing to the control member 176. In an embodiment, such tracing is shown on the cuff display screen 184. The second inflatable portion 166 is then released and the oximetry tracing is transmitted to the recording device 204. The record produced by the recording device 204 is then entered in the patient's chart. In an embodiment, the radial check device 150 can perform a reverse Barbeau test to check for radial flow for patients with repeat radial procedures.

Figure 12:
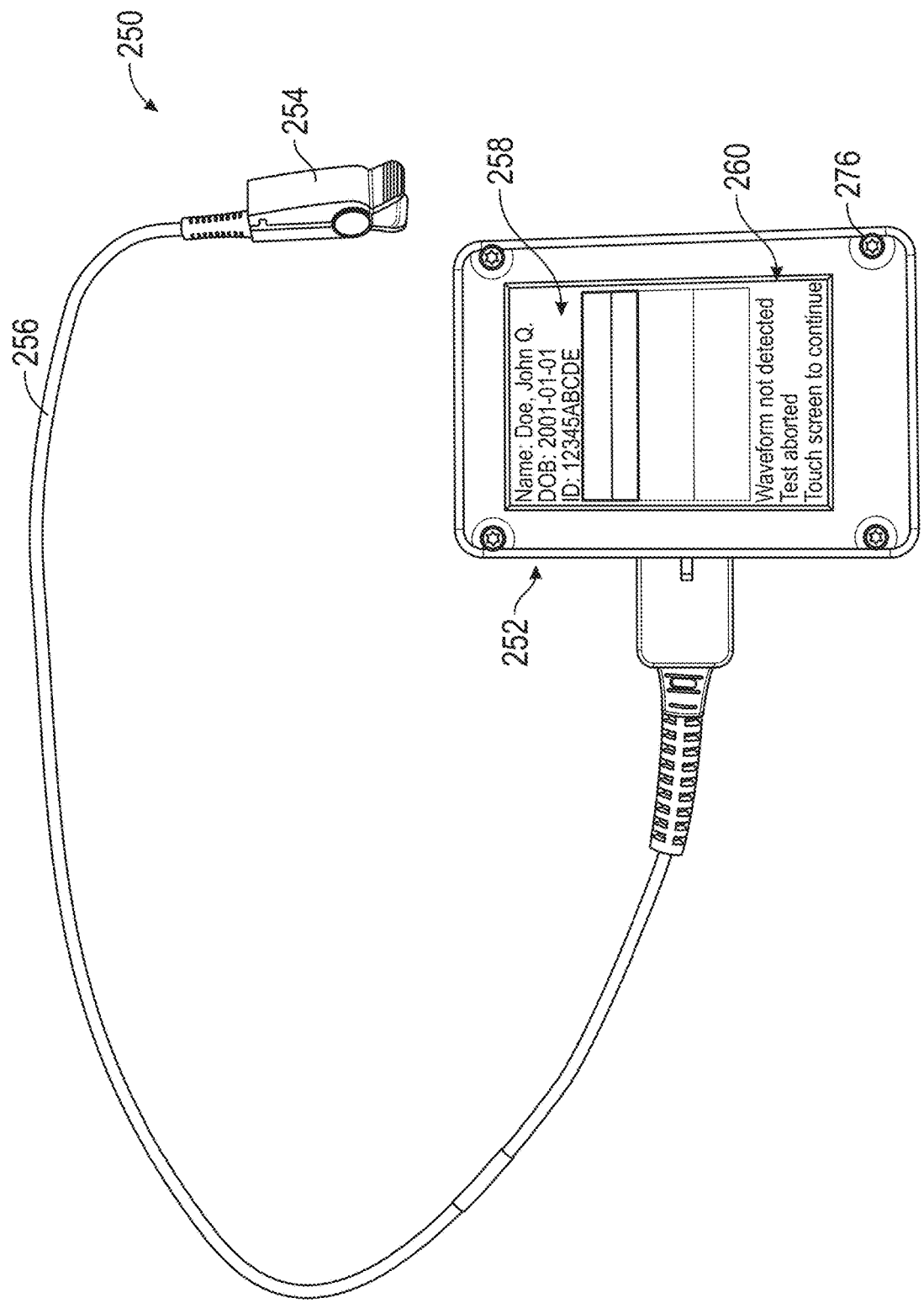
FIG. 12 is a perspective view of an embodiment of the radial check device.

Referring now to FIGS. 12-18, an alternative embodiment of a radial check device 250 is shown and described. As shown in FIG. 12, the radial check device 250 includes a readout device 252 and a pulse oximeter 254 configured for positioning on a patient's finger, such as an index finger or thumb, where the pulse oximeter 254 is operatively connected to a readout device 252. As shown in FIG. 12, the pulse oximeter 254 is connected to the readout device 252 by cable 256. The readout device 252 includes hardware, software, and/or firmware configured to control operation of the pulse oximeter 254, and receive, display, and store pulse readings from the pulse oximeter 254. Measurements from the pulse oximeter 254 can be displayed through a graphical user interface 258 on a display screen 260 of the readout device 252. Further, the readout device 252 produces an electronic record of the data, and can enter the data in a patient's electronic chart.

Figure 13A:
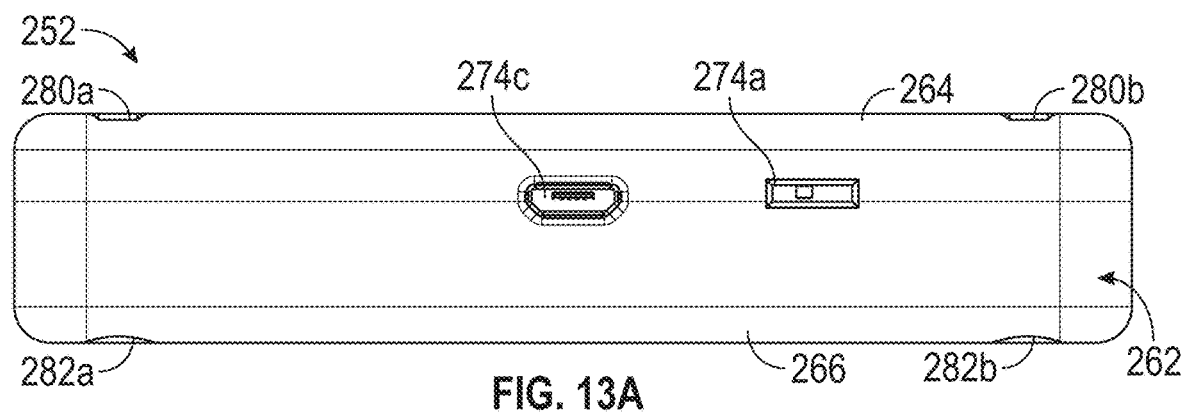
FIGS. 13A-13B are side elevational views of the readout device of an embodiment of the radial check device.
Figure 13B:
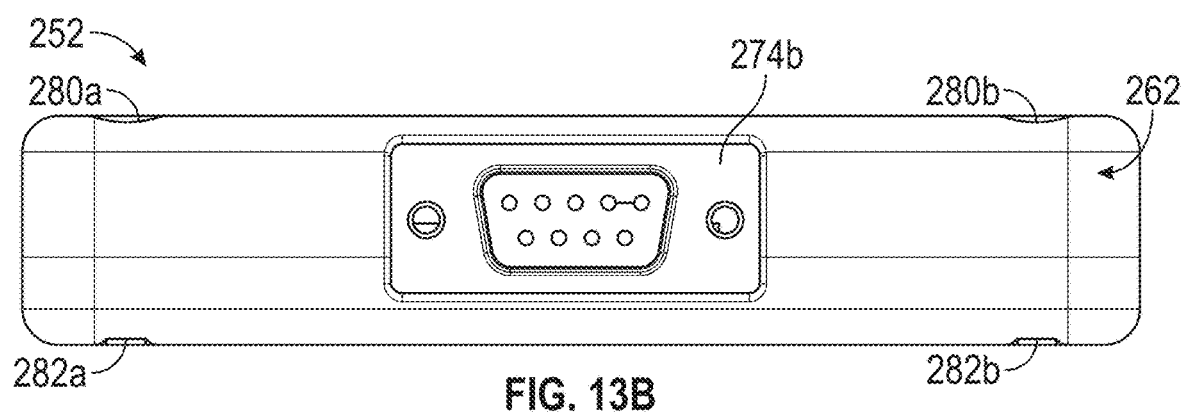
Figure 14:
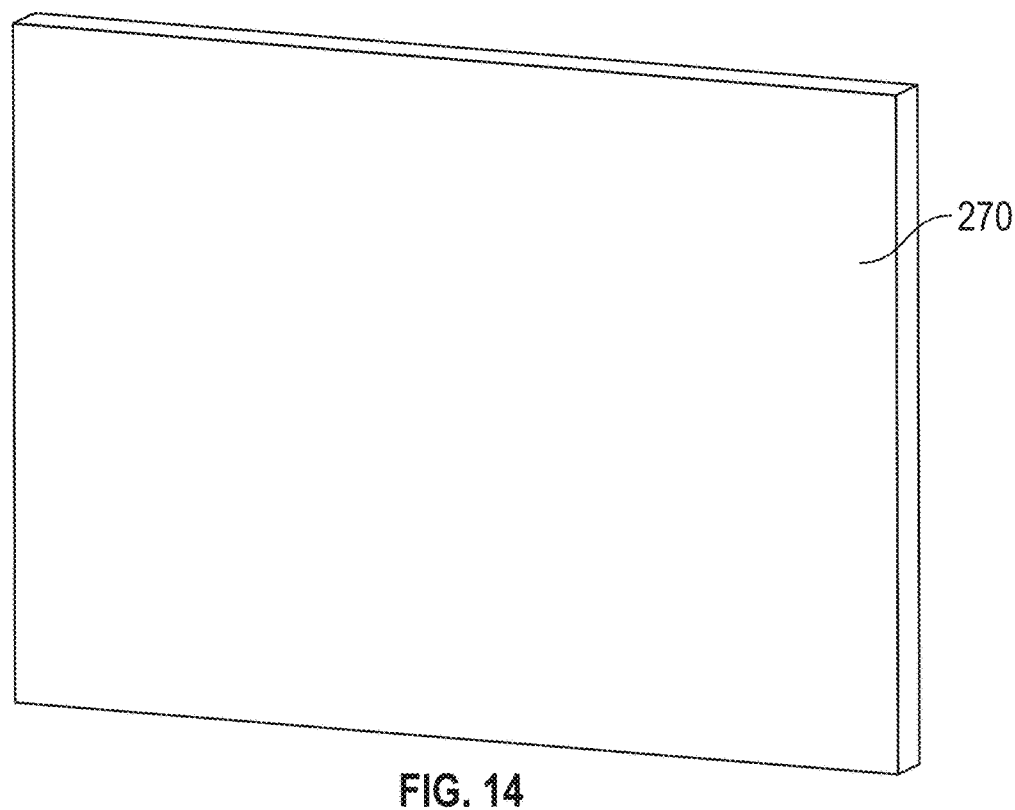
FIG. 14 is a perspective view of a rechargeable battery for the readout device.

The readout device 252, depicted in FIGS. 13A-13B, is generally composed of a housing 262 having a top cover 264 and a bottom cover 266, a display screen 260, a circuit board 268, and a battery 270. The top cover 264 and the bottom cover 266 are connected and together house the display screen 260, circuit board 268, and battery 270, which are operatively connected to produce a graphical user interface 258 displayable on the display screen 260, and read and store readings from the pulse oximeter 254. The top cover 264 includes an opening through which the display screen 260 is accessible to the user. The readout device 252 as illustrated can be powered by a rechargeable battery, such as the battery 270 depicted in FIG. 14, or by disposable batteries. The rechargeable battery 270 can be charged while the device 250 is connected to a computer via a suitable connection, such as a USB connection. Alternatively, the readout device 252 can be powered by an external power source, in which case there is no need for a battery 270 within the housing 262. The readout device 252 can be connected to the pulse oximeter 254 via any suitable connection, including hardwired or wireless (e.g., Bluetooth) connections. The non-limiting example radial check device 250 depicted in FIGS. 12-18 is shown with a hardwired connection between the readout device 252 and the pulse oximeter 254.

The readout device 252 generally includes a number of ports 274 for connection to extraneous devices. In addition to a suitable port 274 for connecting via wire to the pulse oximeter 254, the readout device 252 may include one or more additional ports 274 for connection to other devices or systems such as, but not limited to, monitors, tablets, computers, and phones, as well as internet connections. The readout device 252 may further include a headphone jack, and in such embodiments may be configured to play audible sounds that convey information about the measured pulse oximetry data. As shown in FIGS. 13A-13B, the readout device 252 may include a USB port 274a, for receiving a removable storage device such as a flash drive, a nine-pin serial port 274b, for connecting the readout device 252 to the pulse oximeter 254, and an HDMI port 274c, for connecting the readout device 252 to an external monitor or the like. However, the number and identity of ports 274 on the readout device 252 are customizable based on the desired use environment. For example, the readout device 252 may include one or more additional ports 274 for firewire connections, Ethernet connections, audio connections, and the like. Furthermore, the readout device 252 may include a power connector configured to power the readout device 252 through a normal power outlet instead of, or as a backup to, the battery 270.

Figure 15:
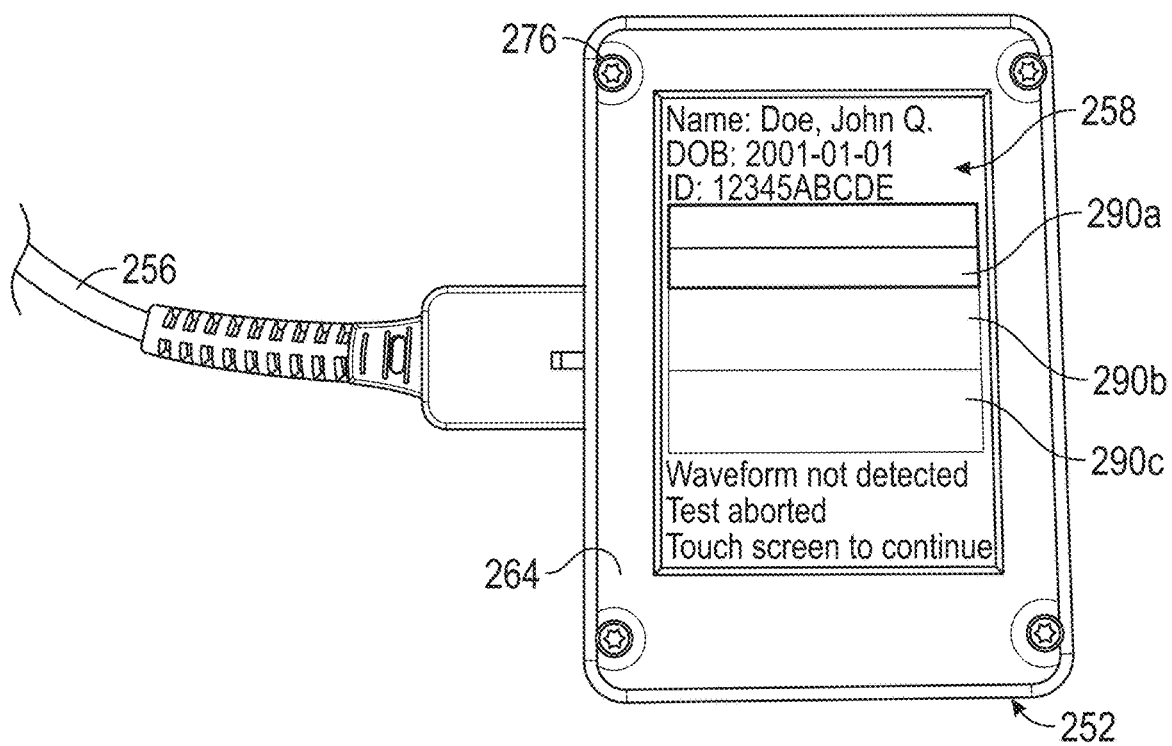
FIG. 15 is view of the graphic user interface (GUI) displayed on the readout device of an embodiment of the radial check device.

As seen in FIG. 15, the graphical user interface 258 on the readout device 252 can display information such as the name of the patient, the patient's date of birth, an identification number for the patient, and any other patient-specific information desired. Further, the graphical user interface 258 can display real-time data gathered from the pulse oximeter 254, such as in three rectangular boxes 290a, 290b, 290c, as depicted in FIG. 15. The rectangular boxes 290a, 290b, 290c can be highlighted when displaying real-time pulse readings for the user's convenience. For example, in FIG. 15, the top rectangular box 290a is shown highlighted with an oximetry trace displayed therein.

Figure 16:
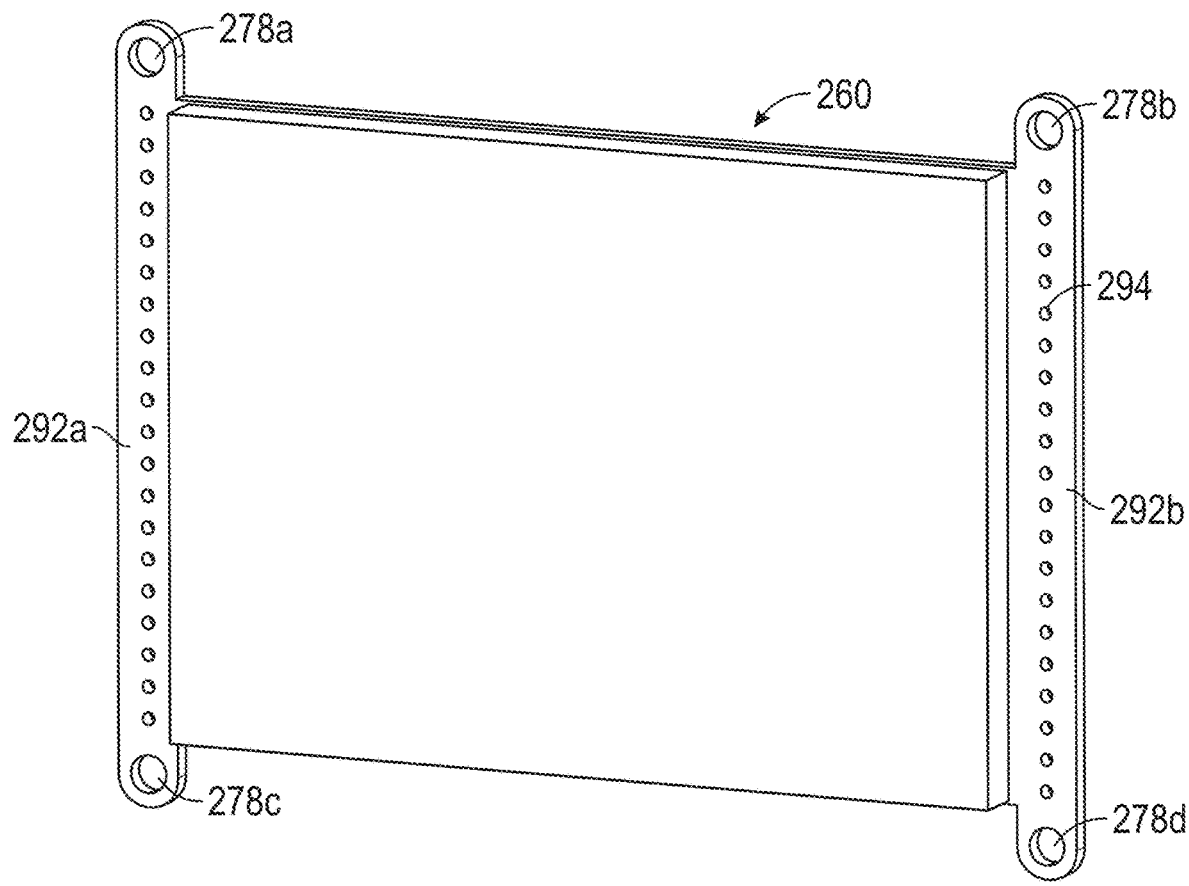
FIG. 16 is an elevational view of the display screen on the readout device.
Figure 17A:
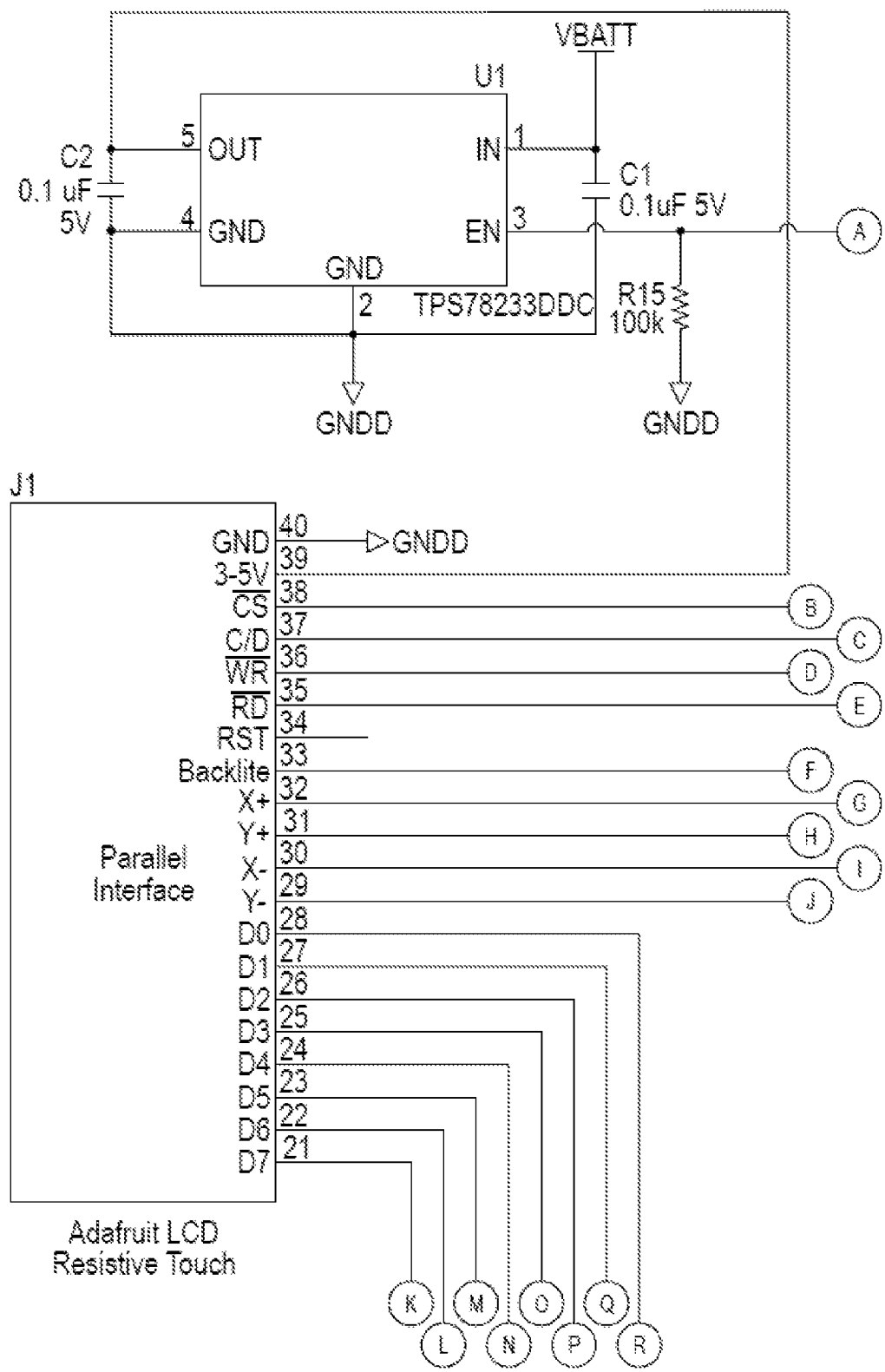
FIGS. 17A-17J are non-limiting schematics of circuit board layouts for use in the readout device of an embodiment of the radial check device.
Figure 17B:
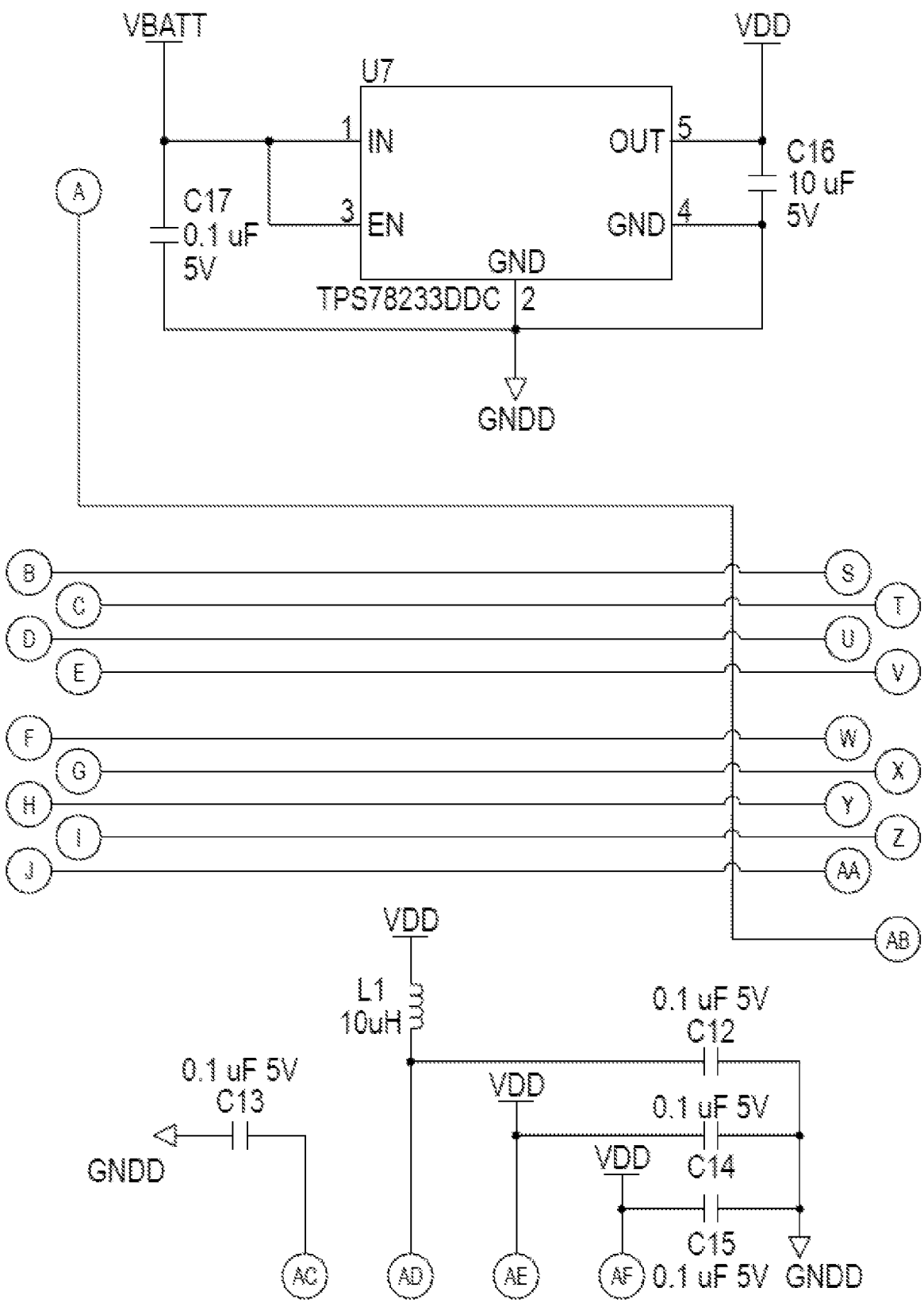
Figure 17C:
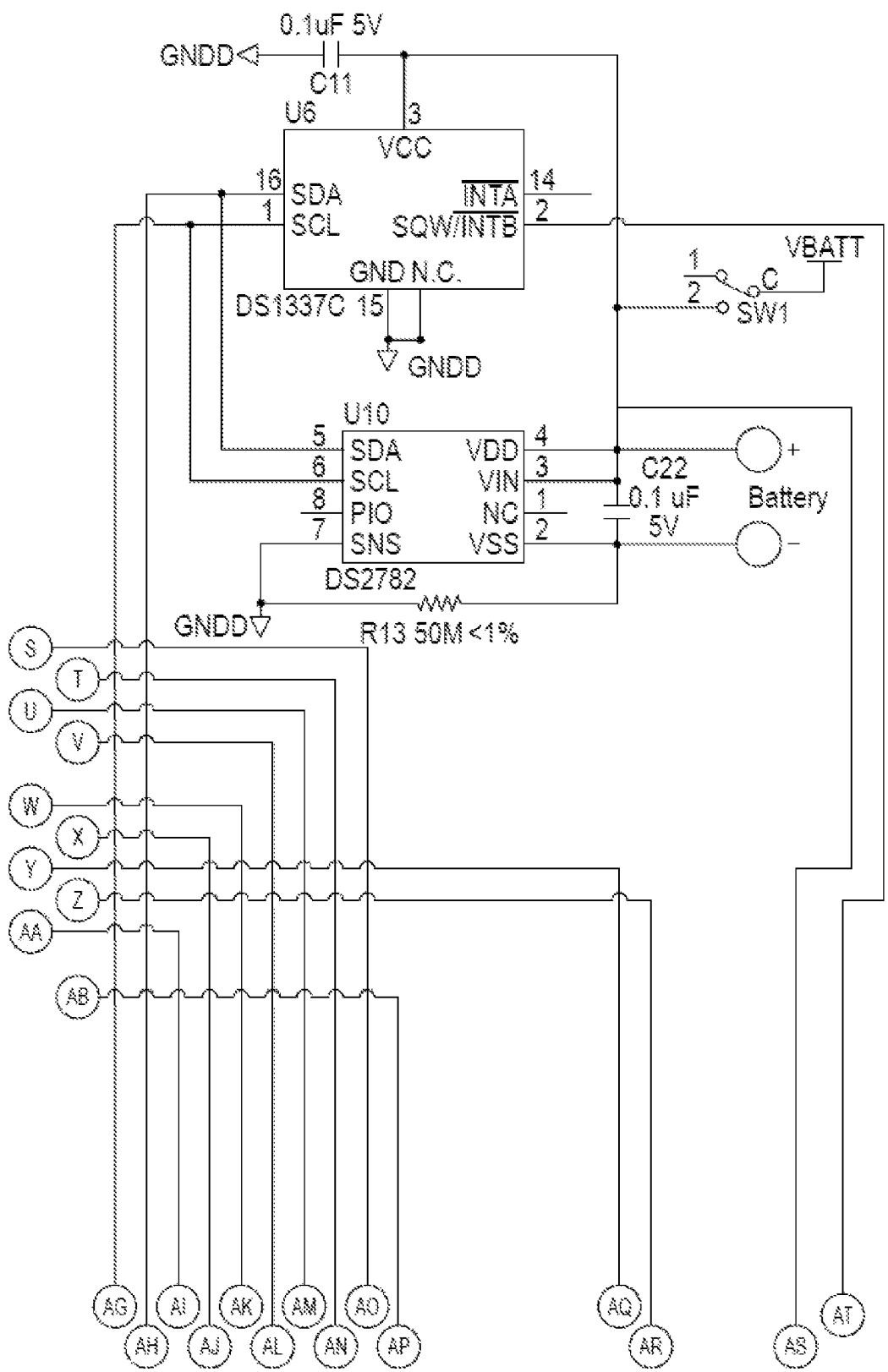
Figure 17D:
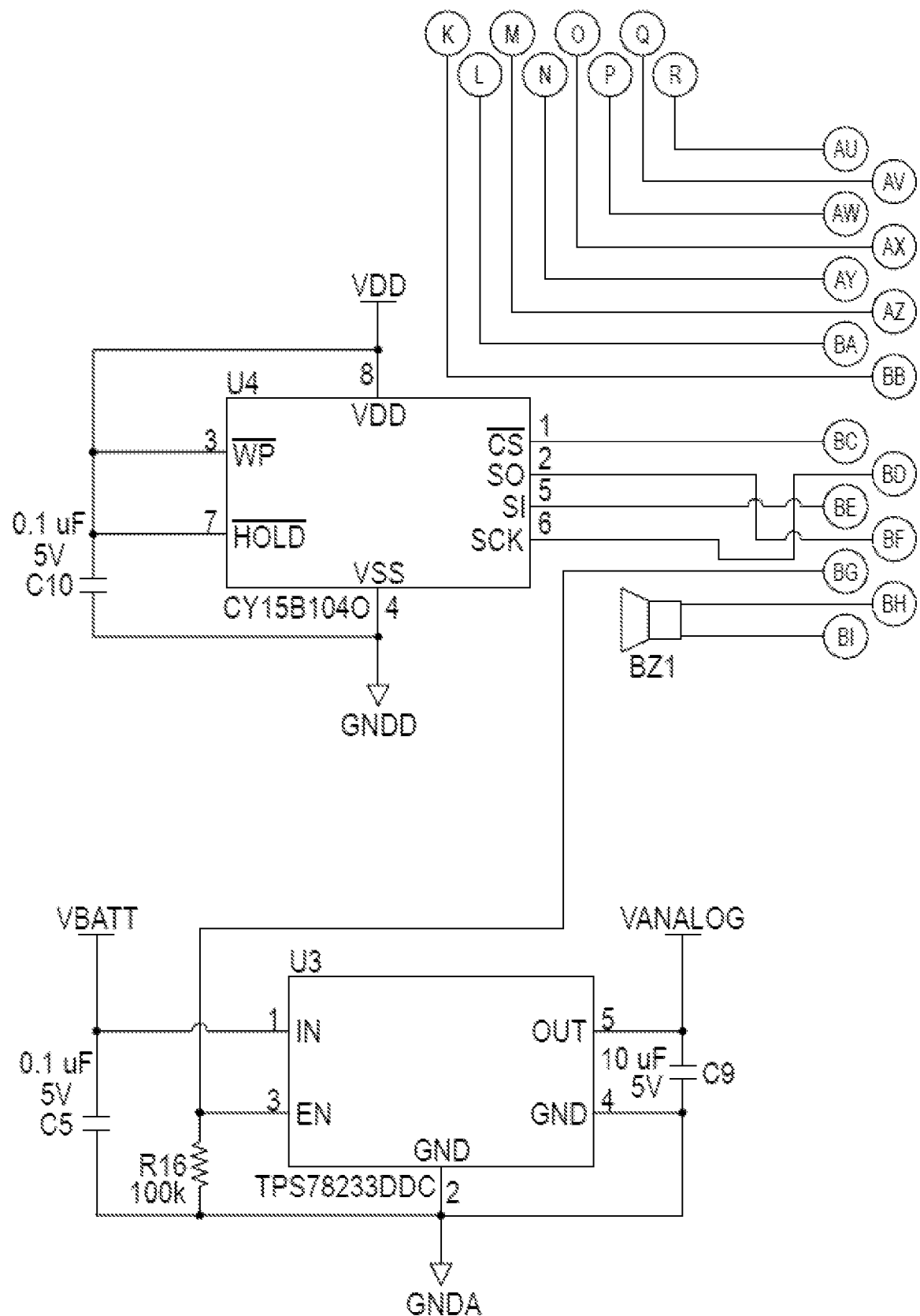
Figure 17E:
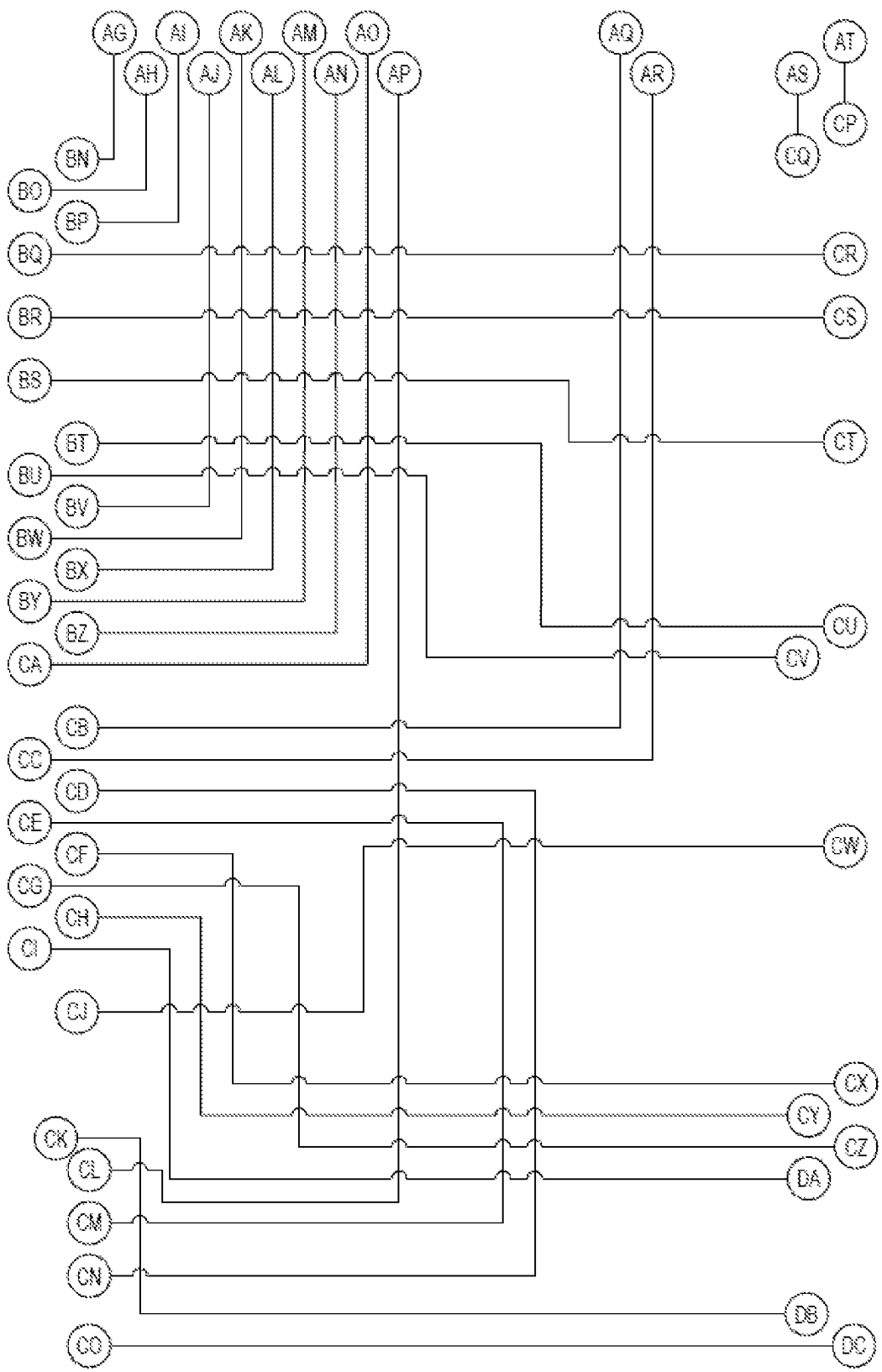
Figure 17F:
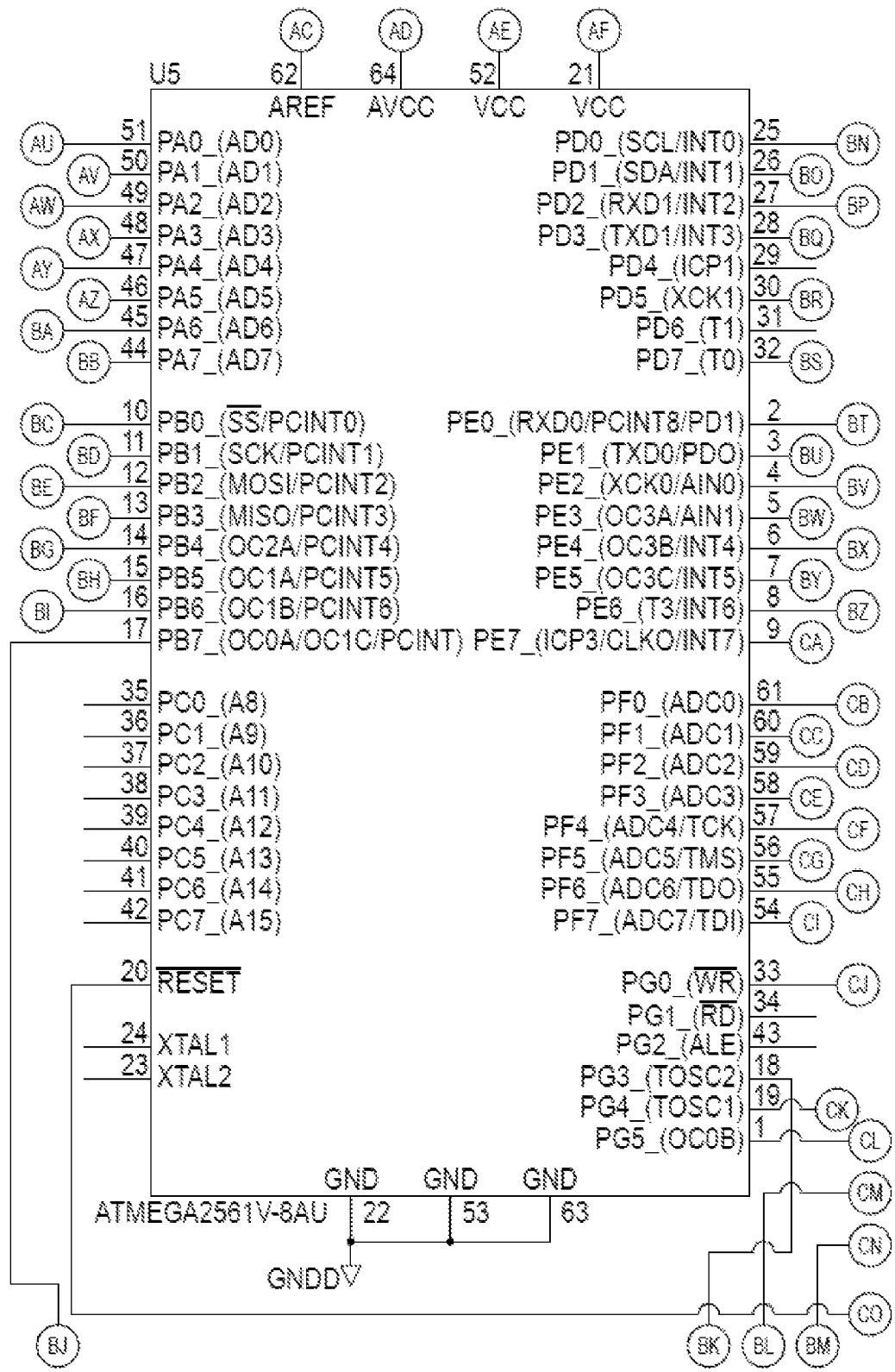
Figure 17G:
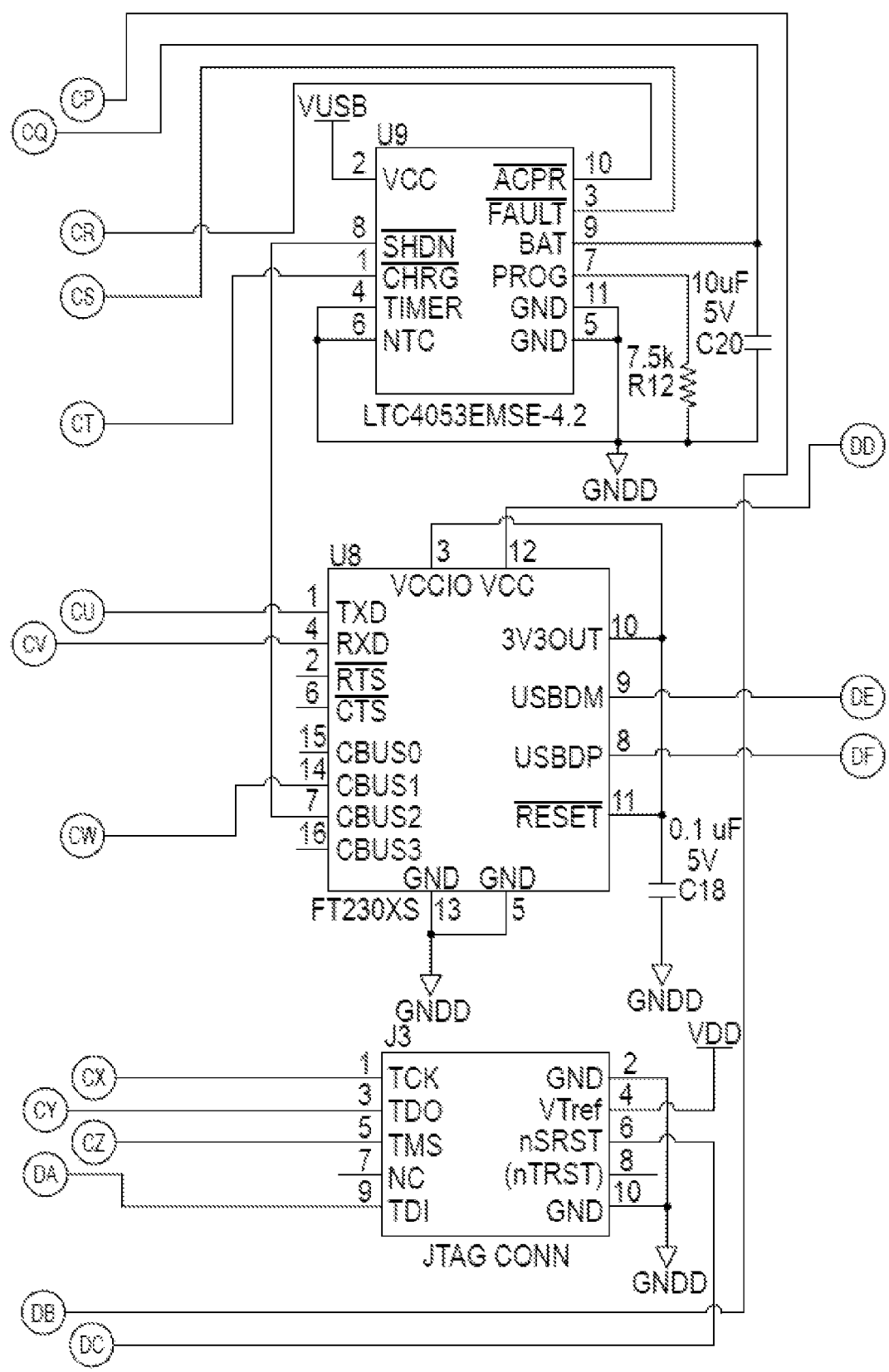
Figure 17H:
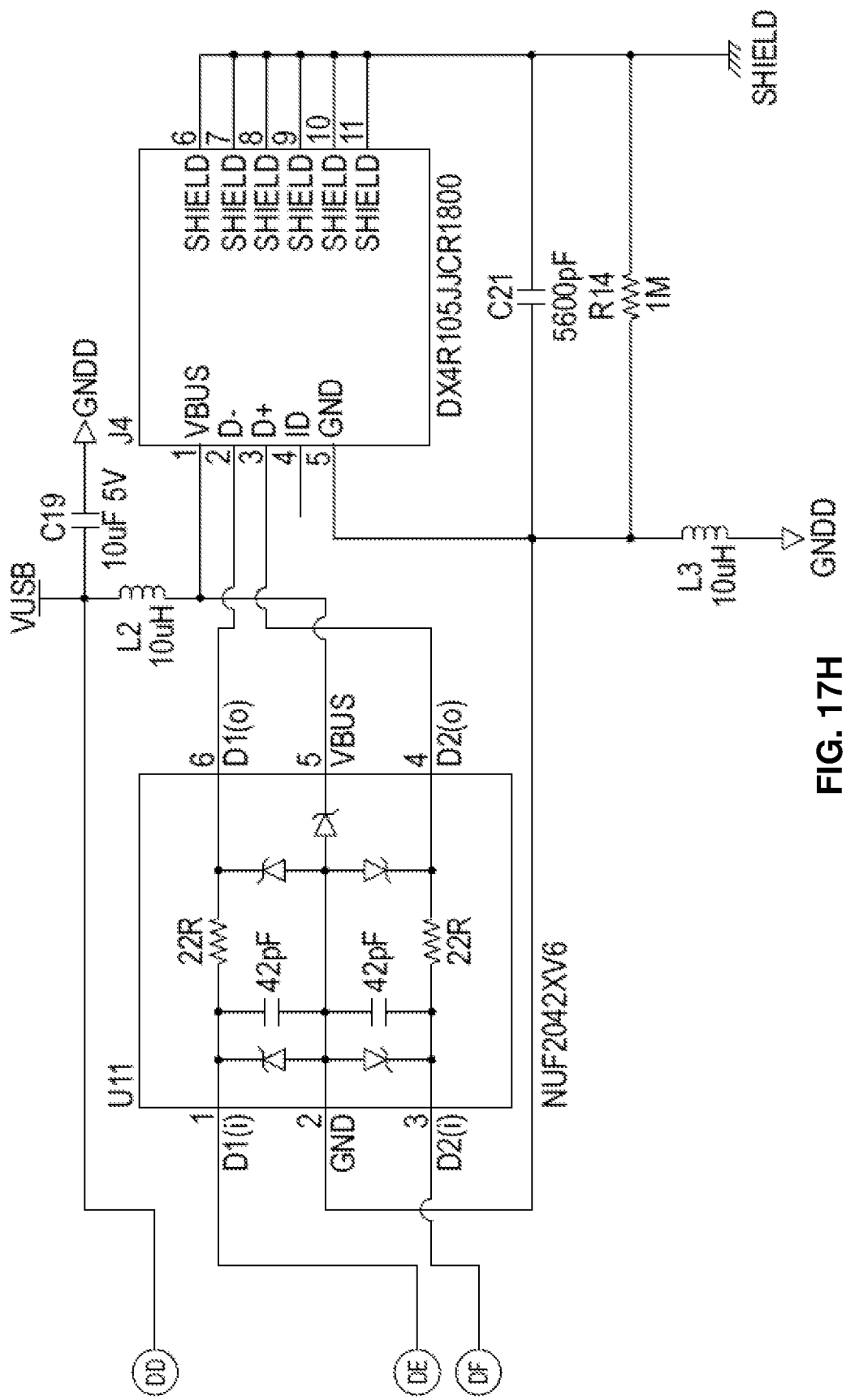
Figure 17I:
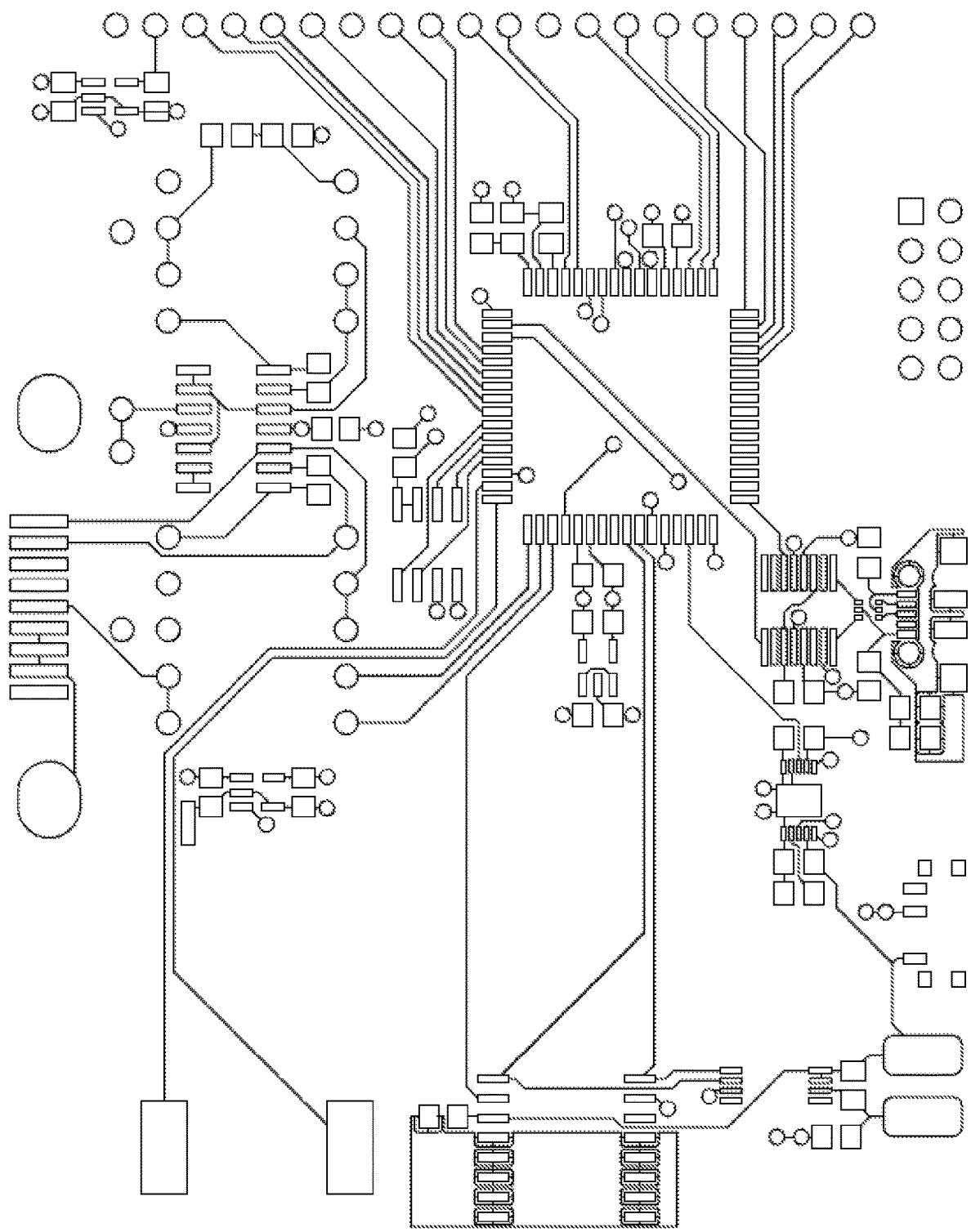
Figure 17J:
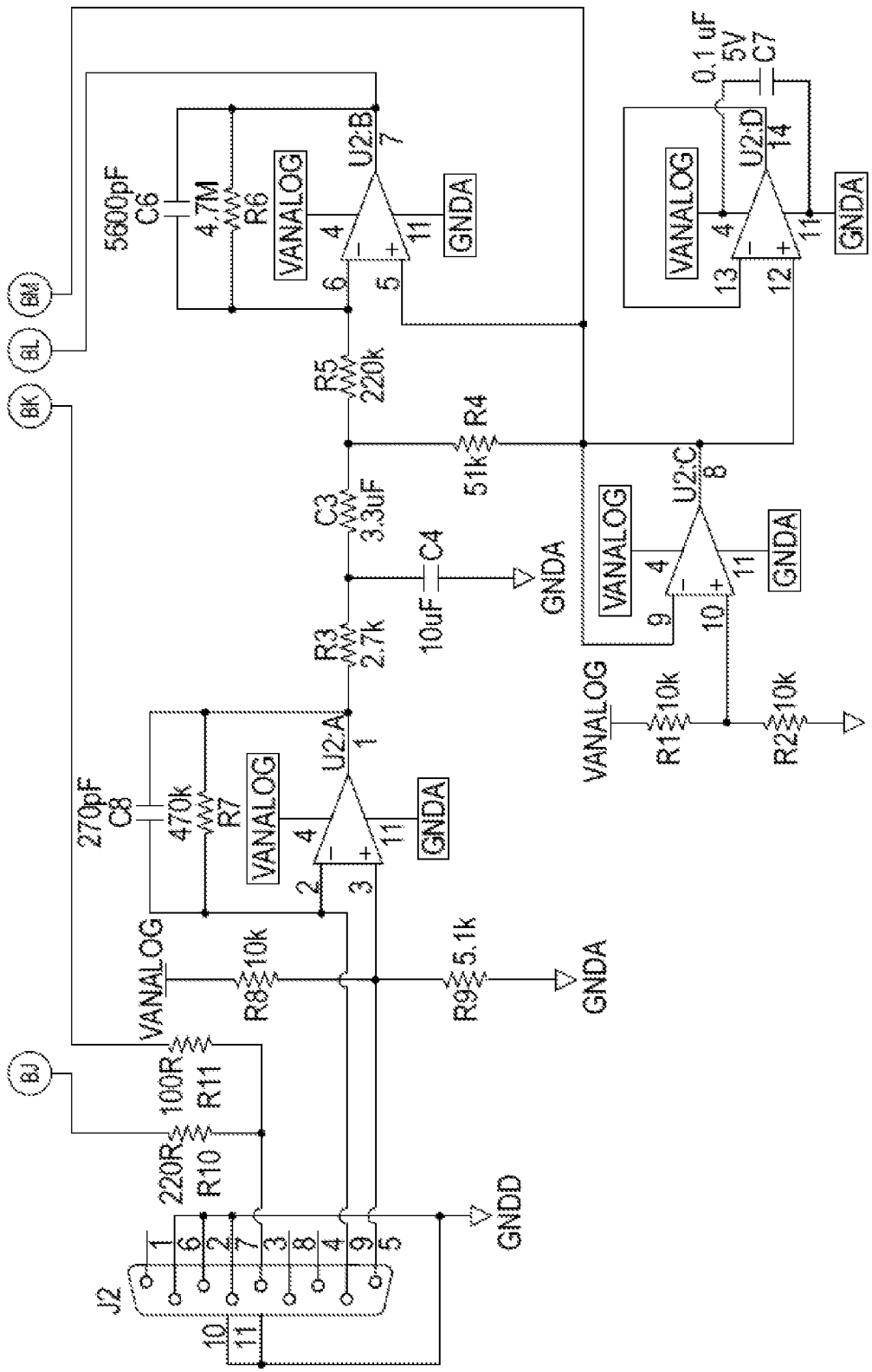

The display screen 260 is generally a touchscreen, such that the graphical user interface 258 is displayed on a touchscreen where a user may enter commands and control the pulse oximeter 254 or data recording functions of the readout device 252 by selecting the appropriate options on a touchscreen menu. The display screen 260, depicted in FIG. 16, can be fabricated from any suitable touchscreen monitor material, and may be, for example, a thin-film-transistor liquid-crystal display. The touchscreen 260 can be secured by screws 276 between the top cover 264 and bottom cover 266 of the housing 262. As shown in FIG. 16, the display screen 260 has two side flanges 292a, 292b which include screw holes 278a, 278b, 278c, 278d that align with screw holes 280a, 280b in the top cover 264 of the housing 262 and screw holes 282a, 282b in the bottom cover 266 of the housing 262. The side flanges 292a, 292b may further include additional screw holes 294, as depicted in FIG. 16, for alternative or additional connections between the display screen 260 and the housing 262.

The touchscreen display 260 may be configured to allow use of a special stylus or one or more fingers. Though a touchscreen-type of display is described for exemplary purposes, and a touchscreen-type of display is generally more convenient for the user, it is understood that the display screen 260 need not be a touchscreen. Rather, the device 252 may be configured to be controlled through a mouse, external touchpad, voice commands, or the like, instead of touchscreen menu options.

Figure 18A:
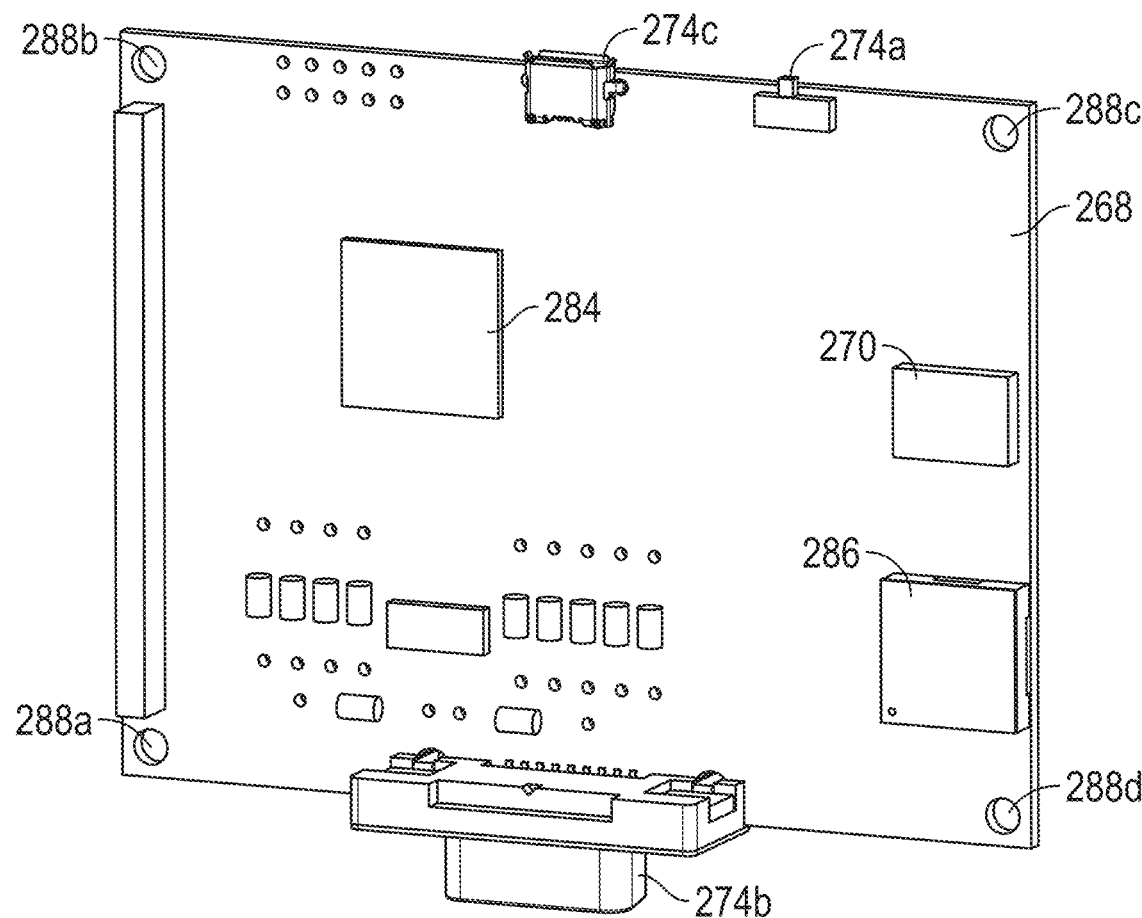
FIGS. 18A-18B are views of a circuit board of the readout device.
Figure 18B:
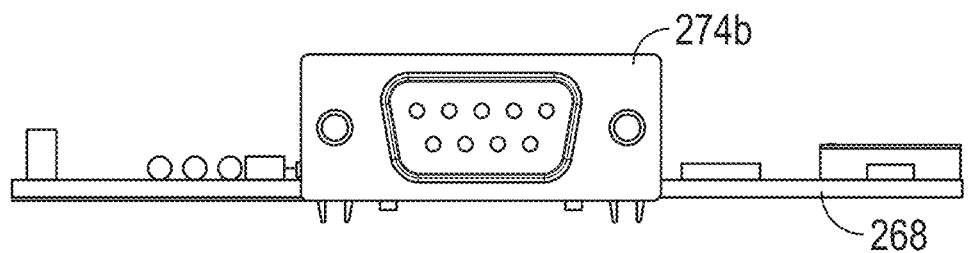

FIGS. 17A-17J depict non-limiting schematics of example layouts for the circuit board 268 in the readout device 252. FIGS. 18A-18B show views of an example circuit board 268 incorporating the schematic designs shown in FIGS. 17A-17J. Though these schematics are shown for illustrative purposes, it is understood that other circuit board layouts, including layouts that utilize multiple circuit boards, are possible and entirely encompassed within the present disclosure. The example circuit board 268 depicted in FIGS. 18A-18B includes conventional circuit board components, such as a central processing unit 284, and a memory component 286, such as a ferroelectric RAM. The readout device 252 is capable of storing pulse measurements in the memory 286. These stored measurements can be accessed by a user along with the patient information, date, time, and status of each test performed. Similarly, the memory 286 can be cleared so as to remove stored records from the radial check device 250.

The circuit board 268 includes screw holes 288*a*, 288*b*, 288*c*, 288*d* that align with the screw holes 280*a*, 280*b* of the top cover 264 and screw holes 282*a*, 282*b* of the bottom cover 266, as well as with the screw holes 278*a*, 278*b*, 278*c*, 278*d* of the display screen 260. Thus, the circuit board 268 is physically secured to the display screen 260 and the top cover 264 and the bottom cover 266 of the housing 262 with screws 276 or the like. The circuit board 268 and the display screen 260 are operatively connected through suitable electronic connections.

The radial check device 250 depicted in FIGS. 12-18 does not include an occlusion cuff in operative connection with the oximeter 254 or readout device 252. Instead, this embodiment of the radial check device 250 is intended for use with any means of occluding the radial and/or ulnar arteries. This can include manual occlusion with the practitioner's hands, the use of a conventional blood pressure cuff, or the use of an occlusion cuff such as an occlusion cuff similar to the occlusion cuff 12 depicted in FIGS. 1-2, the occlusion cuff 52 depicted in FIGS. 3-6, or the occlusion cuff 152 depicted in FIGS. 9-11, though without operative connections to the readout device 252 or the pulse oximeter 254. In each case, the practitioner will be responsible for properly occluding the radial and/or ulnar arteries. However, the absence of an occlusion cuff in operative connection with the oximeter 254 or the readout device 252 renders this embodiment of the radial check device 250 more versatile because it provides the user with the freedom to implement their preferred method of artery occlusion.

The graphical user interface 258 displayed in the embodiment of the radial check device 250 depicted in FIGS. 12-18 can be programmed and customized in a variety of manners to produce an operational system. The system includes the pulse oximeter 254, the readout device 252, and the graphical user interface 258, where the system is configured to (i) prompt a user, through the graphical user interface 258, to attach the pulse oximeter 254 to the patient; (ii) detect from the pulse oximeter 254, display on the graphical user interface 258, and record in memory 286, a baseline pulse of the patient over a first period of time; (iii) prompt the user, through the graphical user interface 258, to occlude radial and ulnar arteries of the patient; (iv) detect from the pulse oximeter 254, display on the graphical user interface 258, and record in memory 286, an absent pulse of the patient over a second period of time following occlusion of the radial and ulnar arteries of the patient; (v) prompt the user, through the graphical user interface 258, to release the radial and ulnar arteries of the patient; (vi) detect from the pulse oximeter 254, display on the graphical user interface 258, and record in memory 286, a restored pulse of the patient over a third period of time; and (vii) display on the graphical user interface 258 each of the baseline pulse, the absent pulse, and the restored pulse so as to allow the user to compare the baseline pulse, the absent pulse, and the restored pulse. For ease of use, the first, second, and third periods of time are typically equal, though they need not be. The graphical user interface 258 can display all three measured pulses on the same screen for easy comparison.

A non-limiting example operation of the system, described through device operation, GUI displays, and methods of using the device, will now be described with reference to various operational modes of the device referred to as introductory mode, idle mode, sleep mode, detecting baseline pulse mode, recording baseline pulse mode, detecting absent pulse mode, recording absent pulse mode, release ulnar artery mode, detecting restored pulse mode, and test complete mode. However, it is understood that the system may be programmed to omit or alter one or more of these operational modes, or to include other operational modes. For example, the system may further include a historical data mode, where the system displays pulse measurements recorded from a particular patient in the past.

In the non-limiting example operation of the system, when the readout device 252 is first powered on, the readout device 252 proceeds to introductory mode, where the graphical user interface 258 displays an introduction screen which may include hospital logos, legal disclaimers, copyright notices, simple instructions for users, and the like. The user can turn the readout device 252 to idle mode by touching the appropriate touchscreen menu item.

In idle mode, the readout device 252 displays patient information, three blank pulse waveforms in rectangular boxes 290*a*, 290*b*, 290*c*, and instructions to begin, such as, "Attach sensor to patient and touch screen to begin." Upon a user touching the appropriate touch screen menu item, a serial receive interrupt is enabled and a five-minute countdown begins, after which time the system proceeds to sleep mode if the screen is not touched. However, if the screen is touched during the five-minute countdown, the system proceeds to detecting baseline pulse mode and detects the baseline pulse through the pulse oximeter 254.

In sleep mode, the readout device 252 can be powered off by toggling an on/off switch or selecting the appropriate touch screen menu item. Alternatively, touching the screen 260 or connecting a USB to the readout device 252 transitions the system from sleep mode back to the introduction screen.

In detecting baseline pulse mode, the graphical user interface 258 highlights the top pulse waveform box 290*a*, with a trace drawing of the measured pulse appearing from left to right on the screen in the highlighted box 290*a*. In this mode, the middle waveform box 290*b* and the bottom waveform box 290*c* are displayed as blank. During this time, the graphical user interface 258 displays an informative status message such as, "Detecting baseline pulse, please wait." The user can stop the measurement by disabling the serial receive interrupt through the appropriate touch screen menu item. Otherwise, the system reads the pulse from the oximeter 254 measurements, draws the pulse in the top waveform box 290*a* from left to right on the screen, wrapping, and adjusts the amplifier gain and LED brightness to maximize pulse amplitude without clipping. The pulse is displayed as a function of time. If a pulse is detected with stable amplitude and frequency for five seconds, the system proceeds to recording baseline pulse mode. If 30 seconds elapse without detecting a pulse, the graphical user interface 258 displays a message such as, "Test failed, baseline pulse not detected." If no pulse is detected, the system records an incomplete test result to memory 286 (such as the ferroelectric RAM inside the readout device 252, or a removable flash drive inserted in the readout device 252 during operation), and proceeds to idle mode. Alternatively, instead of recording the incomplete test result to memory, the system may transmit the incomplete test result to an external server.

In recording baseline pulse mode, the graphical user interface 258 highlights the top pulse waveform box 290*a* with a trace drawing from left to right in the box, and with a status message such as, "Recording baseline pulse, please wait." During this time, the graphical user interface 258 displays a countdown for five seconds. The system reads the pulse from the oximeter 254 measurements, draws the pulse waveform in the top waveform box 290*a* from left to right, wrapping, and records the pulse waveform to memory. The pulse is displayed as a function of time. If the pulse is lost, the system proceeds to detecting baseline pulse mode. If five seconds elapse with a pulse present, the system proceeds to detecting absent pulse mode.

In detecting absent pulse mode, the graphical user interface 258 highlights a middle pulse waveform box 290*b,* with a trace drawing from left to right in the middle pulse waveform box 290*b.* The top pulse waveform box 290*a* retains the measured baseline pulse waveform, but is no longer highlighted. The bottom pulse waveform box 290*c* is blank. The graphical user interface 258 displays a message prompting the user to occlude the radial and ulnar arteries, such as, "Occlude radial and ulnar arteries." The system reads the pulse from the pulse oximeter measurements, and draws the measured pulse in the middle waveform box 290*b* from left to right, wrapping. The pulse is displayed as a function of time. If a pulse is absent for five seconds, the system proceeds to recording absent pulse mode. If 30 seconds elapse with the pulse still present, the system records an incomplete test to memory, displays a status message such as, "Test failed, arteries not occluded", and proceeds to idle mode.

In recording absent pulse mode, the graphical user interface 258 highlights the middle pulse waveform box 290*b,* with a trace drawing from left to right in the middle pulse waveform box 290*b.* The graphical user interface 258 displays an informative status message such as, "Recording absent pulse, please wait", and displays a five-second countdown. The system reads the pulse from the pulse oximeter 254 measurements, draws the measured pulse in the middle waveform box 290*b* from left to right, wrapping, and records the pulse waveform to memory. The pulse is displayed as a function of time. If the pulse returns, the system proceeds to detecting absent pulse mode. If five seconds elapse with a pulse still absent, the system proceeds to release ulnar artery mode.

In release ulnar artery mode, the graphical user interface 258 highlights a bottom pulse waveform box 290*c,* with a trace drawing from left to right in the bottom pulse waveform box 290*c.* The top pulse waveform and the middle pulse waveform remain in respective top and middle pulse waveform boxes 290*a,* 290*b,* though the top and middle pulse waveform boxes 290*a,* 290*b* are no longer highlighted. The graphical user interface 258 displays a message such as, "Release ulnar artery in 5 . . . 4 . . . 3 . . . 2 . . . 1 . . . " while conducting a five-second countdown. During this five-second time period, the system reads the pulse from the pulse oximeter 254 measurements, and draws the measured pulse in the bottom waveform box 290*c* from left to right, wrapping. The pulse is displayed as a function of time. When the countdown reaches zero, the readout device 252 audibly beeps and the system proceeds to recording restored pulse mode. If a pulse returns before the countdown reaches zero, the system proceeds to detecting absent pulse mode.

In detecting restored pulse mode, the graphical user interface 258 highlights the bottom pulse waveform box 290*c,* with a trace drawing from left to right in the bottom pulse waveform box 290*c.* The graphical user interface 258 also displays a status message such as, "Detecting pulse restoration." The system reads the pulse from the pulse oximeter 254 measurements, and draws the measured pulse in the bottom waveform box 290*c* from left to right, wrapping. The pulse is displayed as a function of time. The system records the pulse waveform to memory 286, and begins a 20-second countdown which is displayed on the graphical user interface 258. If a pulse is detected, the system begins a five-second countdown. If the 20 seconds elapse without a pulse detected continuously for five seconds, the graphical user interface 258 displays a failure message such as, "Pulse not detected", the system records a negative test complete to memory 286, and the system proceeds to test complete mode. If, on the other hand, a pulse is detected and five seconds elapse with the pulse present, the graphical user interface 258 displays a success message such as, "Pulse restoration detected", the system records a positive test complete to memory, and the system proceeds to test complete mode.

In test complete mode, the graphical user interface 258 retains all three pulse waveforms on display in the respective boxes 290*a,* 290*b,* 290*c,* and retains the test result message (i.e., either the failure message or the success message). The graphical user interface 258 also displays completion messages such as, "Touch screen to finish/save", and "Long press to cancel/restart". Once in test complete mode, the system enables a serial receive interrupt and begins a five-minute timer. If five minutes elapses without the screen being touched, or upon the screen being touched during the five minutes, the system proceeds to idle mode. Alternatively, if the screen is long-pressed as prompted, the system restarts by returning to introduction mode.

Other possible functions of the system include reporting battery conditions, receiving and implementing firmware updates from an external source, and communicating with the patient's electronic medical records. The particular functions of the system are not intended to be limiting. Rather, the system is versatile and can be customized for desired uses.

By way of non-limiting examples, the radial check device 10, 50, 150, or 250 can be used in all places of a hospital or other healthcare facility (e.g., cardiac catheterization lab, vascular interventions lab, pediatric and/or adult intensive care unit, or pre-operative anesthesia unit) in which the radial artery of a patient is used for cannulation. The present disclosure provides embodiments of a relatively simple medical device that a healthcare professional can utilize to access the ulnar and/or radial flow of a patient, and then place the documentation generated by the device in the paper and/or electronic chart of the patient. As will be appreciated by those skilled in the art, the present disclosure establishes a new standard of pre-procedural care for patients undergoing any type of radial artery canalization.

Certain embodiments of the systems, devices, and methods disclosed herein are defined in various examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A radial check device comprising:
    a pulse oximeter adapted to generate an oximetry tracing of a patient upon occlusion or release of an artery of the patient;
    an occlusion cuff adapted for attachment to the patient and having an inner surface engaging the patient and an outer surface, the occlusion cuff having a portion disposed at the inner surface, the portion of the occlusion cuff expandable between a first position releasing the artery of the patient and a second position occluding the artery of the patient, wherein the occlusion cuff is in operative communication with the pulse oximeter; and
    a readout device operatively connected to the pulse oximeter to generate a record of the oximetry tracing and display the record on a graphical user interface.

2. The radial check device of claim 1, wherein the pulse oximeter has a display screen.

3. The radial check device of claim 1, wherein the readout device includes a control system adapted to control the pulse oximeter.

4. The radial check device of claim 1, wherein the readout device produces an electronic record.

5. The radial check device of claim 1, wherein the pulse oximeter is hardwired to the readout device.

6. The radial check device of claim 1, wherein the pulse oximeter is wirelessly connected to the readout device.

7. The radial check device of claim 1, wherein the readout device comprises one or more ports configured to connect to an external display system, monitor, computer, tablet, or phone.

8. The radial check device of claim 1, wherein the readout device is configured to control the function of the pulse oximeter.

9. The radial check device of claim 8, wherein the readout device is configured to control the function of the pulse oximeter via a touchscreen menu on a graphical user interface.

10. A method of measuring ulnar flow comprising the steps of:
    occluding radial and ulnar arteries independently from each other;
    releasing the ulnar artery;
    generating an oximetry tracing with a pulse oximeter; and
    displaying the oximetry tracing on a readout device through a graphical user interface, wherein the readout device includes a control system adapted to control the pulse oximeter;
    wherein the graphical user interface prompts a user when to occlude and release the radial and ulnar arteries through a display screen.

11. The method of claim 10, wherein the radial and ulnar arteries are occluded manually.

12. The method of claim 10, wherein a user can input patient information through the graphical user interface.

13. A system for checking ulnar and radial flow, the system comprising:
    a readout device having a display screen, wherein a graphical user interface is displayable on the display screen;
    a pulse oximeter operatively connected to the readout device and configured to read a pulse of a patient and communicate the pulse to the readout device;
    wherein the system is configured to:
        (i) prompt a user, through the graphical user interface, to attach the pulse oximeter to the patient;
        (ii) detect from the pulse oximeter, display through the graphical user interface, and record in memory, a baseline pulse of the patient over a first period of time;
        (iii) prompt the user, through the graphical user interface, to occlude radial and ulnar arteries of the patient;
        (iv) detect from the pulse oximeter, display through the graphical user interface, and record in memory, an absent pulse of the patient over a second period of time following occlusion of the radial and ulnar arteries of the patient;
        (v) prompt the user, through the graphical user interface, to release the radial and ulnar arteries of the patient;
        (vi) detect from the pulse oximeter, display through the graphical user interface, and record in memory, a restored pulse of the patient over a third period of time; and
        (vii) display through the graphical user interface each of the baseline pulse, the absent pulse, and the restored pulse simultaneously through the display screen after the third period of time so as to allow the user to compare the baseline pulse, the absent pulse, and the restored pulse.

14. The system of claim 13, wherein the system is configured to adjust amplifier gain and LED brightness to maximize the baseline pulse amplitude without clipping.

15. The system of claim 13, wherein the first, second, and third periods of time are the same.

16. The system of claim 13, wherein the graphical user interface allows the user to input patient information.

17. The system of claim 13, wherein the memory comprises a ferroelectric RAM inside the readout device.

18. The system of claim 13, wherein the memory comprises a removable flash drive inserted in the readout device during operation.

19. The system of claim 13, wherein the readout device comprises one or more ports configured to connect the readout device to an external monitor, memory device, or power source.

20. The system of claim 13, wherein the readout device is powered by a rechargeable battery.

* * * * *